US007113450B2

(12) United States Patent
Plancon et al.

(10) Patent No.: US 7,113,450 B2
(45) Date of Patent: Sep. 26, 2006

(54) WEARABLE ELECTRONIC DEVICE WITH MULTIPLE DISPLAY FUNCTIONALITY

(75) Inventors: Michel G. Plancon, Besancon (FR); Louis M. Galie, Newtown, CT (US); Herbert Schwartz, Wurmberg (DE); Gerhard Stotz, Eisingen (DE)

(73) Assignee: Timex Group B.V., (NL)

( * ) Notice: Subject to any disclaimer, the term of this patent is extended or adjusted under 35 U.S.C. 154(b) by 106 days.

(21) Appl. No.: 10/441,417

(22) Filed: May 20, 2003

(65) Prior Publication Data

US 2004/0233788 A1 Nov. 25, 2004

(51) Int. Cl.
*G04B 47/00* (2006.01)
*G04B 47/06* (2006.01)
*A61B 5/02* (2006.01)

(52) U.S. Cl. ............................ 368/10; 368/11; 368/80; 600/502; 600/523

(58) Field of Classification Search ................ 368/110, 368/10, 11, 223, 47, 46, 52, 80; 73/379.09; 600/528
See application file for complete search history.

(56) References Cited

U.S. PATENT DOCUMENTS 3,216,261 A * 11/1965 Brown et al. ................. 74/1.5
4,407,295 A 10/1983 Steuer et al. ............... 128/670
4,650,344 A * 3/1987 Allgaier et al. ............... 368/47
4,845,485 A * 7/1989 Pace ......................... 340/7.38
4,855,942 A * 8/1989 Bianco ....................... 702/160
4,860,268 A * 8/1989 Allgaier et al. ............... 368/47
5,105,396 A * 4/1992 Ganter et al. ................. 368/47
5,224,059 A * 6/1993 Nitta et al. .................... 73/384
5,299,126 A 3/1994 Spraker ....................... 364/420
5,538,007 A 7/1996 Gorman ....................... 128/710
5,659,521 A 8/1997 Amano ........................ 368/10
5,721,713 A * 2/1998 Bornand ...................... 368/10
5,737,246 A 4/1998 Furukawa et al. .......... 364/562
5,771,399 A * 6/1998 Fishman ...................... 710/72
5,802,016 A * 9/1998 Kubota et al. ................ 368/11
5,905,460 A * 5/1999 Odagiri et al. ......... 342/357.06
5,960,366 A * 9/1999 Duwaer ................... 455/556.1
6,269,054 B1 7/2001 Truini ......................... 368/29
6,278,659 B1 * 8/2001 Yokouchi ..................... 368/11
6,304,518 B1 * 10/2001 O'Neill ....................... 368/47
6,314,058 B1 11/2001 Lee ............................ 368/10
6,356,856 B1 3/2002 Damen et al. .............. 702/160
6,751,164 B1 * 6/2004 Sekiguchi .................... 368/80
6,761,478 B1 * 7/2004 Schmiedchen et al. ..... 368/101
7,035,170 B1 4/2006 Narayanaswami et al.
2001/0043514 A1 * 11/2001 Kita ........................... 368/281

OTHER PUBLICATIONS

Bulova Technical Letter, Model No. 96C21, Book No. 563M, pp. 1-3.
Citizen Eco-Drive Instruction Manual, pp. 62-131.

* cited by examiner

*Primary Examiner*—Vit W. Miska
(74) *Attorney, Agent, or Firm*—Carmody & Torrance LLP

(57) ABSTRACT

A wearable electronic device for conveying information in an analog manner at least in part by the use of at least one display hand positioned on the dial side of a dial, wherein the wearable electronic device uses the display hand(s) to convey information that is stored in the controller of the device and/or provided by sensors and/or an external transmitter. An actuation mechanism, preferably a stepper motor, is used to rotate the display hands in the clockwise and/or counter-clockwise directions in predefined increments to convey the information.

5 Claims, 17 Drawing Sheets

WEARABLE ELECTRONIC DEVICE WITH MULTIPLE DISPLAY FUNCTIONALITY

BACKGROUND OF THE INVENTION

This invention relates generally to wearable electronic devices, such as timepieces, and in particular, to an electronic device, such as for example and not limitation, a watch, that has multiple display functionality. More specifically, the electronic device of the present invention provides unique constructions and methodologies for displaying information with the use of hands, such as that found in analog watches (i.e. in an "analog manner").

Originally, watches were typically viewed merely as a device for telling time or providing other time related information. Over the years, watches have become the means by which information, other than time information, could be presented to the wearer.

For example, U.S. Pat. No. 5,659,521 ("Amano") describes a watch with a multifunction analog display particularly designed to display time information and biorhythms. Described therein are the use of "small watches" that are able to display the features of the biorhythm along with the display of the current time, and a separate condition display scale and condition display hand is provided therefor. In a related patent, U.S. Pat. No. 6,269,054 ("Truini") describes the use of separate analog displays that correspond to one's intelligence, emotion and body cycles, and the hands for these separate displays are described as being "enacted" by the watch movement. It can thus be seen that Truini, as well as conventional chronograph watches, do not describe or suggest rotation of the smaller displays based on "stored data," but rather merely only upon the passage of time. As will become clear below, this is a perceived deficiency in the prior art.

Most displays of non-time related information has been incorporated into the digital watch. For example, U.S. Pat. No. 5,299,126 describes an electronic tide watch comprising a memory for storing a table of tide times, heights, and geographic offsets, an input circuit for entering times, dates, and geographic offsets, a processing circuit for identifying stored tide information corresponding to a specified time and date, and a display for showing selected tide times and heights.

The use of watches to digitally display information to a user regarding external conditions are also known. For example, U.S. Pat. No. 5,737,246 describes an electronic wrist watch with water depth measuring capability including an LCD panel and display screen for presenting time and water depth, and a display area that illuminate static arrows to indicate depth variations along with the direction of variation.

Another example is set forth in U.S. Pat. No. 6,314,058, which describes a "health watch" for digitally displaying a plurality of information, such as time, atmospheric temperature, body temperature, heart rate and blood pressure.

At least one patent has described the use of a wristwatch with interchangeable sensors for sensing and conveying to a user, through a digital display, information regarding external parameters. Specifically, U.S. Pat. No. 4,407,295 describes a miniature portable physiological parameter measuring system with interchangeable sensors, in which the system can be incorporated into a wrist-worn device having the general configuration of a wristwatch. Through the use of remote sensors, the '295 Patent appears to describe the desirability to enable a wristworn device to monitor heart rates, or other parameters such as lung capacity, temperature, and respiration.

The prior art also describes the use of remotely located sensors that wirelessly transmit heartrate information to a watch. For example, U.S. Pat. No. 5,538,007, describes the transmission of an encoded digital signal from the chestworn transmitter to the wristworn receiver. The receiver receives unit-specific information from the transmitter, which is displayed in the form of a digital number representing the wearer's heart rate. In a similar manner, U.S. Pat. No. 6,356,856 describes a system for measuring the speed of a person while running or walking along a surface. An acceleration sensor located in or on the wearer's shoe provides an acceleration signal which is processed and then transmitted by means of an RF transmitter and received by an RF receiver in a watch. The information, which can include average speed, maximum speed, total distance traversed, calories expended, and heart rate, is then digitally displayed by the runner or walker.

As therefore can be seen, the prior art generally recognizes that a timepiece, such as a wristwatch, can be used to convey non-time related information to a user.

However, the prior art provides such information in a less than desirable format. For example, many of the aforementioned devices display such non "time of day" information digitally. Accordingly, it is extremely difficult to visually appreciate fluctuations in such parameters as they are being displayed. Furthermore, not all users need to have such exacting information, but rather may merely want to ensure they are within a specified range, etc. (e.g. such as a heartrate). For this reason, it is more desirable and effective to use a hand for the display of such information, so that a user can quickly see where his/her heart rate is relative to a chart or scale, especially when the precision of digital representation is unnecessary. Furthermore, studies have shown that, in certain situations, use of a hand to display information may be more desirable than using digital readouts. Still further, at least U.S. Pat. No. 5,659,521 uses a hand that is mounted on the center axis. Such a limitation prohibits more versatile and widely functional display potentials, and impedes the ability, in some constructions, of viewing the time of day simultaneously with the viewing of other displayable information. Lastly, U.S. Pat. No. 6,269,054 appears to describe separate displays that are not independently driven but rather "enacted" by the watch movement, thereby also contributing to the deficiencies in the prior art. As stated above, such a device only describes the movement of the separate display hands based on the passage of time, not on any information stored in the device. Such is also true for conventional chronograph watches.

Accordingly, it can be seen that further advancements in the art are desired. It is believed that the functionality and methodologies to provide the foregoing advantages and achieve the aforementioned objectives, as well as those set forth below, are provided by the present invention.

SUMMARY AND OBJECTIVES OF THE INVENTION

It is thus an objective of the present invention to overcome the perceived-deficiencies in the prior art.

It is another objective and advantage of the present invention to provide an electronic device that clearly displays, and makes easily comprehensible, information relating to data stored in the controller of the device, whether the information be time-based or nontime-based information, and whether or not the information is received from an external source, such as via a telephone link, computer link, wirelessly, or the like.

It is another objective and advantage of the present invention to provide an electronic device that clearly displays, and makes easily comprehensible, information relating to external parameters, as well as time-based or nontime-based information that may be programmed into or otherwise stored in the electronic device.

It is yet another objective and advantage of the present invention to provide an electronic device that can incorporate a wide range of sensor circuits and arrangements for measuring external parameters and have such measurements clearly displayable and easily comprehensible, and to provide an improved method, approach and thus construction to display whatever inputs it receives from sensors.

It is yet another objective and advantage of the present invention to provide an electronic device that can incorporate one or more interconnectable sensors to display various functions and parameters of the human body.

It is still another objective and advantage of the present invention to provide an electronic device that provides a master platform for receiving incoming information from a family of remote sensors and displaying such information in an easy to read manner.

It is a further object and advantage of the present invention to provide a universal platform for displaying information sensed by a host of remote parameter measuring sensors, internal sensors and/or internally stored data in the controller.

It is still a further set of objectives and advantages to provide an improved electronic device that has the rotation of the display hand by not being dependent upon the time of day, such as by providing a display hand that is not mechanically coupled to the hour or minute hands. In this way, the display hand can rotate independently of any rotation of the hour and minute hand. In a specific objective, the data stored may be non-time related data, such as displaying how many pills a user has to still take.

It is a yet another object and advantage of the present invention to provide all of the foregoing in an electronic device, such as a wearable electronic device, such as a timepiece and a wristwatch in particular, that displays the information using hands that are coupled to actuation mechanisms, such as stepper motors.

Further objects and advantages of this invention will become more apparent from a consideration of the drawings and ensuing description.

The invention accordingly comprises the features of construction, combination of elements and arrangement of parts that will be exemplified in the disclosure hereinafter set forth, and the scope of the invention will be indicated in the claims.

To overcome the perceived deficiencies in the prior art and to achieve the objects and advantages set forth above and below, the present invention is, generally speaking, directed to wearable electronic devices, such as electronic timepieces.

In a preferred embodiment, the electronic timepiece comprises at least an hour hand and a minute hand for conveying time of day information and rotatable about a center axis; a dial having a dial side and an actuation mechanism side; and at least one display hand rotatable about an axis other than the center axis and positioned on the dial side of the dial; at least one sensor for sensing at least one parameter external to the electronic timepiece; a controller, operatively coupled to the sensor, for receiving and processing information based on the at least one parameter sensed by the at least one sensor; an actuation mechanism, operatively coupled to the controller, for rotating the at least one display hand in at least one of a clockwise and counterclockwise direction in predefined increments, wherein the increments and direction of the rotation of the at least one display hand are based at least in part on the at least one parameter being sensed by the sensor; wherein the positioning of the display hand as it rotates in the one of the clockwise and counterclockwise directions in predefined increments conveys information relating to the at least one parameter being sensed. In a preferred embodiment, the actuation mechanism comprises a stepper motor that itself comprises a rotor, the stepper motor operatively coupled to the controller, for stepping in at least one of a clockwise and counterclockwise direction in predefined increments based at least in part on the at least one parameter being sensed by the sensor.

In a related embodiment, a wearable electronic device is provided and comprises a dial having a dial side and an actuation mechanism side; and at least one display hand having a first end and a second end, wherein the first end of the display hand rotates about a pivot point spaced apart from a center point of the dial by a fixed distance, and the second end of the display hand sweeps across a portion of the dial side of the dial, wherein the display hand can sweep about an arc; and wherein the display hand has a length from the pivot point that is one of (a) shorter than the fixed distance and (b) longer than the fixed distance; at least one sensor for sensing at least one parameter external to the electronic device; a controller, operatively coupled to the sensor, for receiving and processing information based on the at least one parameter sensed by the at least one sensor; an actuation mechanism, operatively coupled to the controller, for rotating the at least one display hand in at least one of a clockwise and counterclockwise direction in predefined increments, wherein the increments and direction of the rotation of the at least one display hand are based at least in part on the at least one parameter being sensed by the sensor; wherein the positioning of the display hand as it rotates in the one of the clockwise and counterclockwise directions in predefined increments conveys information relating to the at least one parameter being sensed. Here again, in a preferred embodiment, the actuation mechanism comprises a stepper motor that itself comprises a rotor, the stepper motor operatively coupled to the controller, for stepping in at least one of a clockwise and counterclockwise direction in the predefined increments are based at least in part on the at least one parameter being sensed by the sensor.

In yet another related embodiment, the wearable electronic device comprises means, operatively coupled to the controller, for rotating the at least one display hand in at least one of the clockwise and counterclockwise direction in predefined increments.

In yet another embodiment, the wearable electronic device conveys information in an analog manner, where the information is transmitted via a signal being transmitted by a transmitter. Here, the wearable electronic device preferably comprises a receiver for receiving the signal from the transmitter; a controller, operatively coupled to the receiver, for receiving and processing the signal; an actuation mechanism, operatively coupled to the controller, for rotating the at least one display hand in at least one of a clockwise and counterclockwise direction in predefined increments, wherein the increments and direction of the rotation of the at least one display hand are based at least in part on the signal being received by the receiver and transmitted by the transmitter; wherein the positioning of the display hand as it rotates in the one of the clockwise and counterclockwise directions in predefined increments conveys information relating to the signal being received by the transmitter. Here too, in a preferred construction, the actuation mechanism comprises a stepper motor. A system that comprises the transmitter and the wearable electronic device, is also provided.

In yet another embodiment, a wearable electronic device that conveys information in an analog manner may comprise at least an hour hand and a minute hand for conveying time of day information and rotatable about an at least essentially center axis; a dial having a dial side and an opposite side; and at least one display hand rotatable about an axis other than the center axis and positioned on the dial side of the dial; an actuation mechanism, for rotating the at least one display hand in at least one of a clockwise and counterclockwise direction in predefined increments; a controller, operatively coupled to the actuation mechanism, for causing the actuation mechanism to rotate the at least one display hand in at least one of the clockwise and counterclockwise direction in the predefined increments based at least in part on data stored in the controller; wherein the positioning of the display hand as it rotates in the one of the clockwise and counterclockwise directions in the predefined increments conveys information relating to the stored data. Preferably, the rotation of the display hand by the actuation mechanism is not dependent of the time of day. With the rotation of the display hand not dependent on the rotation of the hour or minute hands, the actuation mechanism can rotate the display hand independent of the time of day. If hour and minute hands are coupled to a gearing arrangement, the actuation mechanism will rotate the display hand independently of any rotation of the hour and minute hand. Similar to the other embodiments, the actuation mechanism preferably comprises a stepper motor, which are preferably bi-directional.

In a related embodiment, the wearable electronic device can receive and store data from an external source, and further, can convey information relating to the stored data in an analog manner.

In yet another embodiment, a wearable multimode electronic device is provided and comprises an actuation mechanism, operatively coupled to the at least one display hand, for rotating the at least one display hand in at least one of a clockwise and counterclockwise direction in predefined increments; a controller, operable in a first mode and at least a second mode and operatively coupled to the actuation mechanism, for causing the actuation mechanism to rotate the at least one display hand in at least one of the clockwise and counterclockwise direction in the predefined increments; and a display that is viewable through the at least one window in the dial, wherein the display displays informational indicia corresponding to the mode in which the electronic device is operating, and wherein the informational indicia is changeable based on the mode in which the wearable electronic device is operating; wherein the positioning of the display hand as it rotates in the one of the clockwise and counterclockwise directions in the predefined increments conveys the information and wherein the controller operatively controls the positioning of the hand so that the hand can display the information in the analog manner for each of the at least two modes. In a specific embodiment, the display hand is rotatable about an axis other than the center axis. Preferably, the display is an LCD display and the actuation mechanism comprises a stepper motor. In a specific embodiment, the wearable multimode electronic device includes a receiver and memory for respectively receiving and storing data from an external source.

BRIEF DESCRIPTION OF THE DRAWINGS

The above set forth and other features of the invention are made more apparent in the ensuing Description of the Preferred Embodiments when read in conjunction with the attached Drawings, wherein.

Identical reference numerals in the figures are intended to indicate like parts, although not every feature in every figure may be called out with a reference numeral.

DESCRIPTION OF THE PREFERRED EMBODIMENTS

1. General Overview

Figure 1:
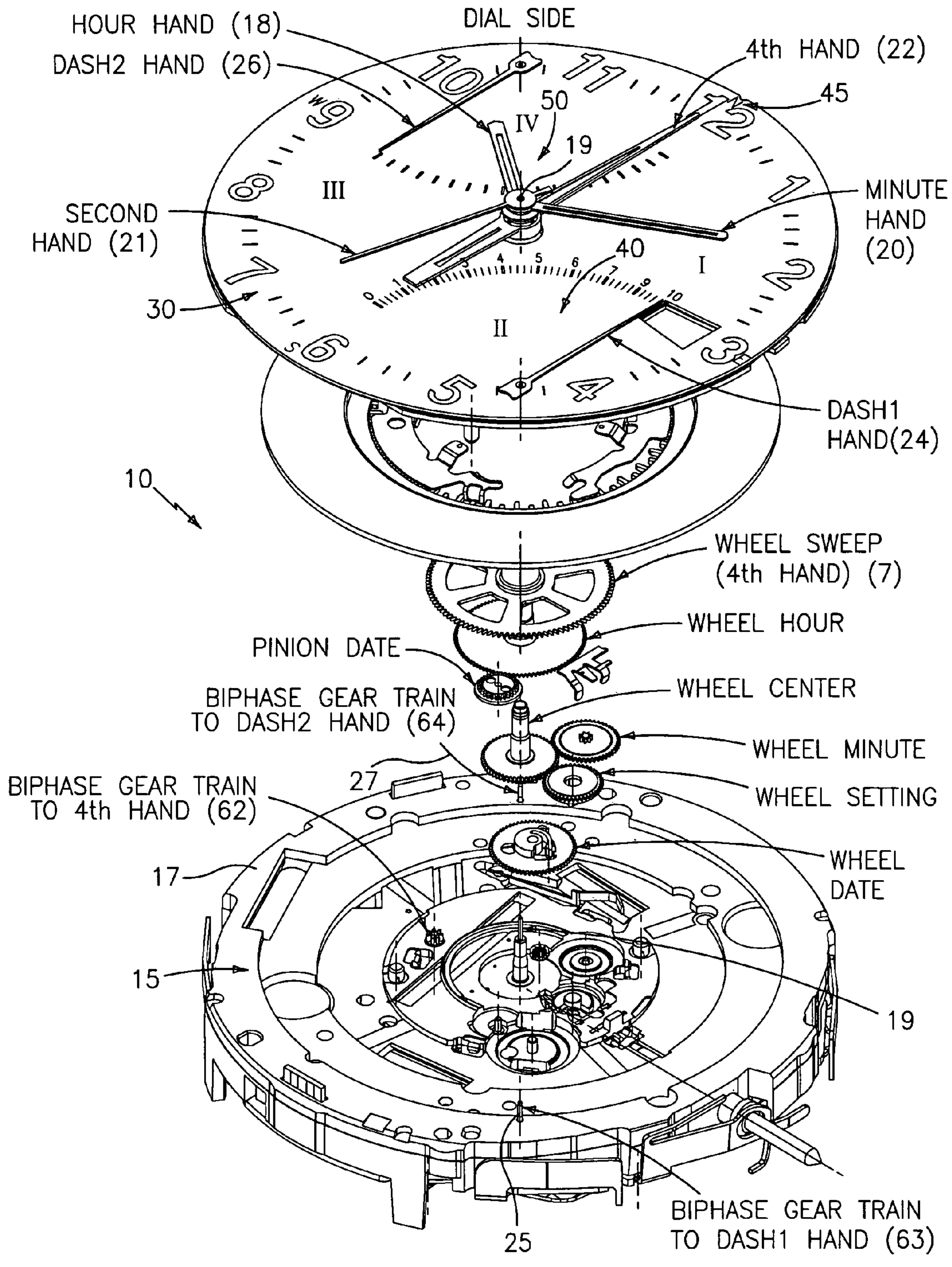
FIG. 1 is an exploded view of an electronic device constructed in accordance with the present invention.
Figure 6:
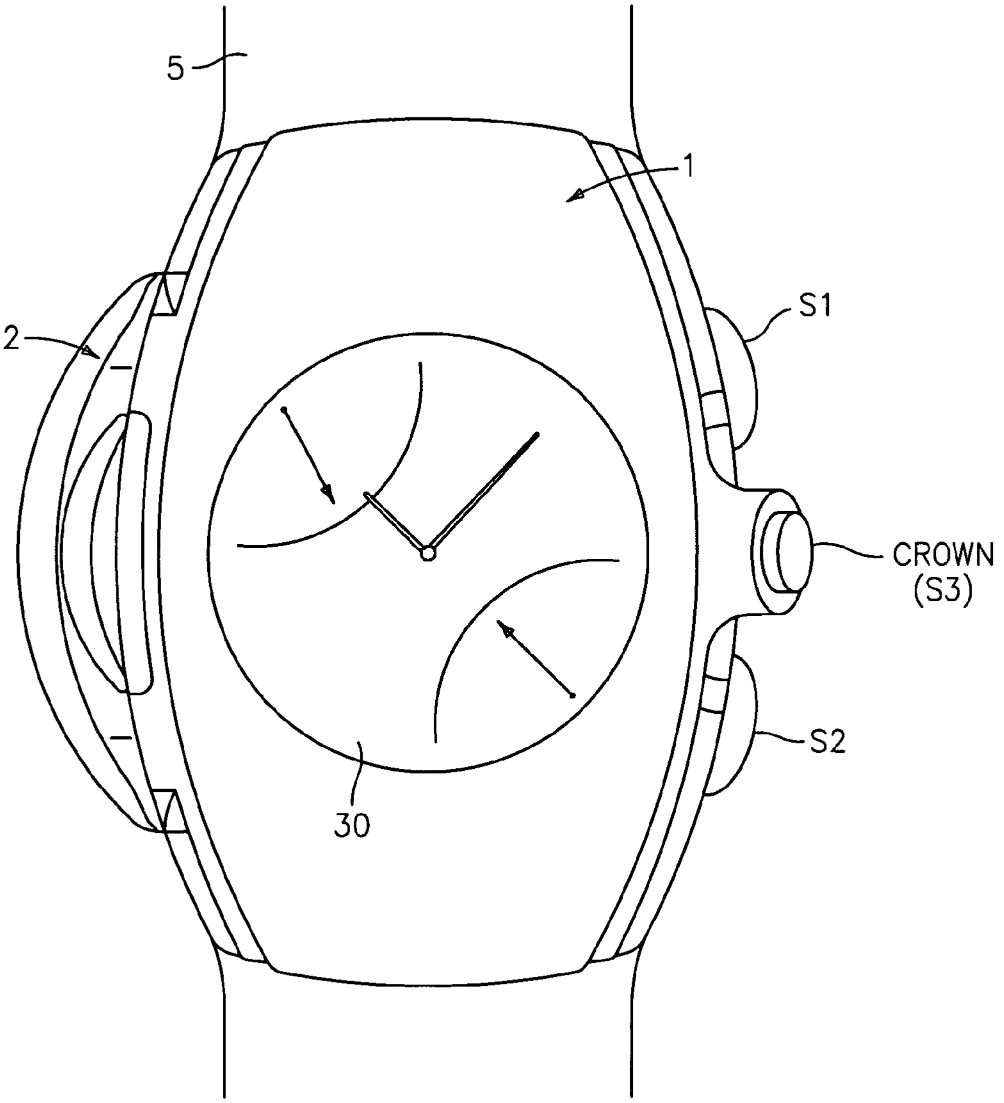
FIG. 6 is a top plan view of a wristwatch illustrating an exemplary sensor circuit that is coupled to the module of the present invention.

Reference is first made generally to FIG. 1, which illustrates an exploded view of an electronic device, generally indicated at 10, constructed in accordance with the present invention. In the preferred construction and as illustrated in FIG. 6, electronic device 10 is a timepiece, such as a wristwatch, generally indicated at 1, which itself will thus comprise other features and parts, namely for example and not limitation, a wrist strap for securing electronic device 10 to a wrist. However, the wrist strap, generally indicated by numeral 5, forms no part of the present invention. Preferably, electronic device 10 is wearable on or about the body.

Generally speaking, electronic device 10 comprises a module, generally indicated at 15, which itself includes a housing 17, in which are disposed many components, the material ones of which pertain to the present invention being hereinafter disclosed. However, it should be understood that the present disclosure will omit, for purposes of brevity, certain basic and very well known concepts regarding the construction of an analog or chronograph watch. For example, the basic construction and arrangements of gears and/or gear trains to rotate a plurality of "standard" hands all supported on a center stem 19, such as an hour hand 18, a minute hand 20 and a "seconds" hand 21, will be omitted as being well within the purview of one skilled in the art. Similarly, disclosure of the manual setting of such hands and the incorporation and construction of a preferred date wheel, are omitted herein as they form no part of the present invention, although reference may be had to application Ser. Nos. 10/334,025; 10/331,827; and 10/342,512, assigned to the present assignee and incorporated by reference as if fully set forth herein, for a description of preferred setting mechanisms and date wheel constructions. However, for purposes of supporting the claims and providing an enabling disclosure, certain parts of such well-known mechanisms will be referenced throughout.

Therefore, the focus of the remaining portions of the specification will be to the best mode known to the inventors and the disclosure necessary to completely enable one skilled in the art to construct an electronic device that incorporates the features and objectives of the present invention.

As illustrated in FIG. 1, electronic device 10 comprises a dial, generally indicated at 30, made of Mylar or another suitable plastic. Dial 30 preferably has numerals, such as 1–12 corresponding to "hours" designations, printed, silk-screened or otherwise formed thereon. Other indicia to assist in telling time may also be provided on dial 30.

For purposes of describing the present invention, dial 30 may be thought of as being divided into quadrants. In this way, the electronic device construction illustrated in FIG. 1 can be seen to be provided with at least two other displays, the first being generally indicated at 40 and generally located in quadrant II, while another display area being generally indicated at 50 and generally located in quadrant IV. However, the locations of such display 40, 50 is one of design choice and only limited by the needed spacing for stepper motors and associated gear trains, since such displays could also be provided in opposing quadrants I & III, or in adjacent ones as well.

Yet another display may be provided on dial 30. This display is illustrated in FIG. 1, but more particularly illustrated in FIG. 11, and uses indicia provided on and about dial 30, such as for example, around the periphery thereof. This display will be denoted display 45, and is exemplary illustrated in FIG. 1 as being associated with compass directions, namely "N," "S," "E" and "W," and in FIGS. 9A–9B as being associated with a heart rate range from 40–200.

Preferably, each display 40, 45 and 50 has its own scale or other information indicia printed, silk-screened or otherwise provided on dial 30, and the demarcations of such scales are one of design choice and a function of the parameter(s) being measured or otherwise displayed, as discussed in greater detail below.

As can also be seen in FIG. 1, electronic device 10 may comprise one or more "display hands" aside from the conventional hour, minute and "seconds" hand. For example, FIG. 1 illustrates (i) a hand 22 also mounted on center stem 19 and associated with display 45, (ii) a "dash1 hand" indicated by the numeral 24 that is mounted on a stem 25 and associated with display 40 and (iii) a "dash2 hand" indicated by the numeral 26 that is mounted on a stem 27 and associated with display 50. As will become clear below, not all hands 22, 24 and 26 need to be provided in each specific embodiment.

For reference, it can be seen that the hour hand and minute hand conveys time of day information and are rotatable about a center axis, and display hands 24 and 26 are rotatable about an axis other than the center axis. For additional reference, it can also be seen that each display hand 24, 26 has a first end and a second end, wherein the first end of each display hand rotates about a pivot point spaced apart from a center point of the dial by a fixed distance, and the second end of the display hand sweeps across a portion of the dial side of the dial, wherein the display hand can sweep about an arc; and wherein the display hand has a length from the pivot point that is one of (a) shorter than the fixed distance and (b) longer than the fixed distance (not shown, but is clear understood as passing through the center point of the display). This reference is important to clearly articulate that display hands 24, 26 are not mounted on the center stem, but rather point inwardly on the dial. This mounting permits the use of additional displays without the need to utilize any of the center-mounted hands, such as the hour and/or minute hands.

2. Hand Movement System

Figure 2:
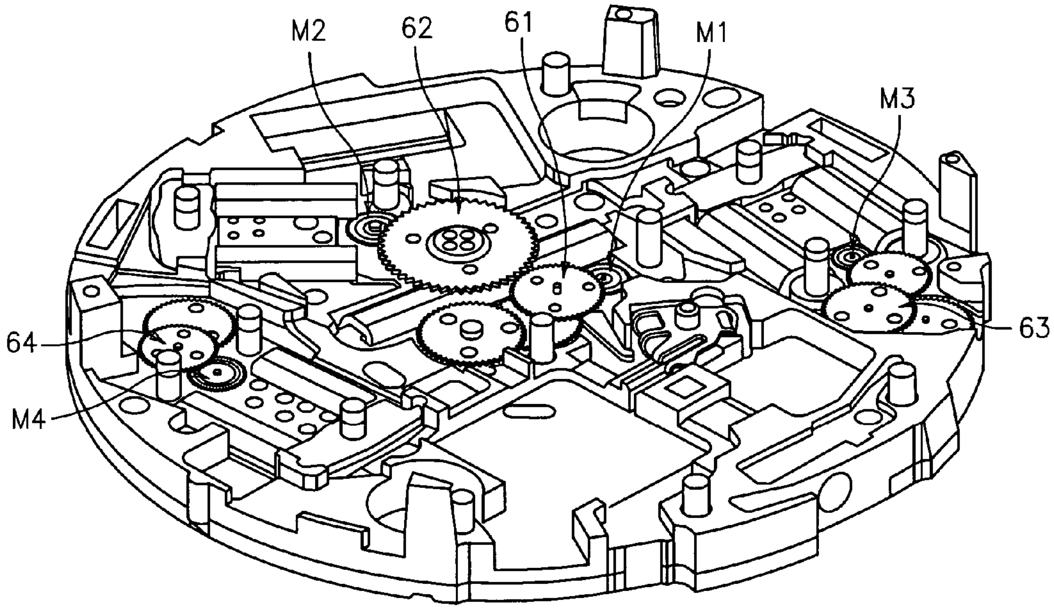
FIG. 2 is a perspective view of the movement side of the module in the electronic device of FIG. 1.

Reference will now also be made to FIG. 2, wherein the embodiment illustrated in FIG. 1 will comprise four stepper motors, each respectively and generally indicated by M1, M2, M3 and M4. One skilled in the art would recognize that varying the number of displays and display hands can vary the number of needed stepper motors, all of which is within the scope of the present invention and disclosure.

As positioned in module 15, motor M1 is provided to rotate hour hand 18, minute hand 20 and "seconds" hand 21 all in a known manner. Specifically, hour hand 18, minute hand 20 and "seconds" hand 21 are coupled to a gear train, generally indicated at 61, for conveying the rotational activity generated by the rotor of motor M1.

In a similar manner, hand 22 is rotated by stepper motor M2, and a gear train generally indicated at 62 is provided to convey the rotational activity generated by the rotor of motor M2 to hand 22. Likewise, hands 24, 26 are each respectively rotated by stepper motors M3 and M4, and a gear train generally indicated at 63 is provided to convey the rotational activity generated by the rotor of motor M3 to hand 24, while a gear train generally indicated at 64 is provided to convey the rotational activity generated by the rotor of motor M4 to hand 26. The construction of the respective gear trains 61–64 are well within the purview of one ordinarily skilled in the art, although certain details thereof are disclosed below and illustrated in FIGS. 12–13 in connection with an autocalibration feature.

Preferably, motors M2, M3 and M4 are bi-directional stepper motors thus being able to rotate in either direction, with as many as two rotor steps per revolution (or 180° per rotor step), and the construction of acceptable stepper motors to functionally operate in this manner are widely commercially available and well within the understanding of those skilled in the art. Preferably, motors M2–M4 are identically constructed. It should also be understood that it is well within the skill of the designer to design an appropriate gearing ratio to provide for the desirable display rotation or movement of display hands 22, 24, 26. That is, it may be desirable for the incremental rotation of the hands to be quire small, thus providing for precise increments and display measurements. For example, in the embodiment, which provides for display hand 22 to measure directional headings (i.e. a compass hand), it is desirable to have very precise movement of hand 22, such as in 1.2° increments. Thus the ratio of the gear train from its associated motor to display hand 22 may be 150. In other examples, such as in the other embodiments disclosed herein with regard to the accuracy of display hands 24 and 26, the ratio of the gear train from the respective motors may be 180, thus providing movement of the display hands in increments of 1°, especially, if by way of example and not limitation, a display scale of 100° degrees is used.

3. Circuit Composition

Figure 3:
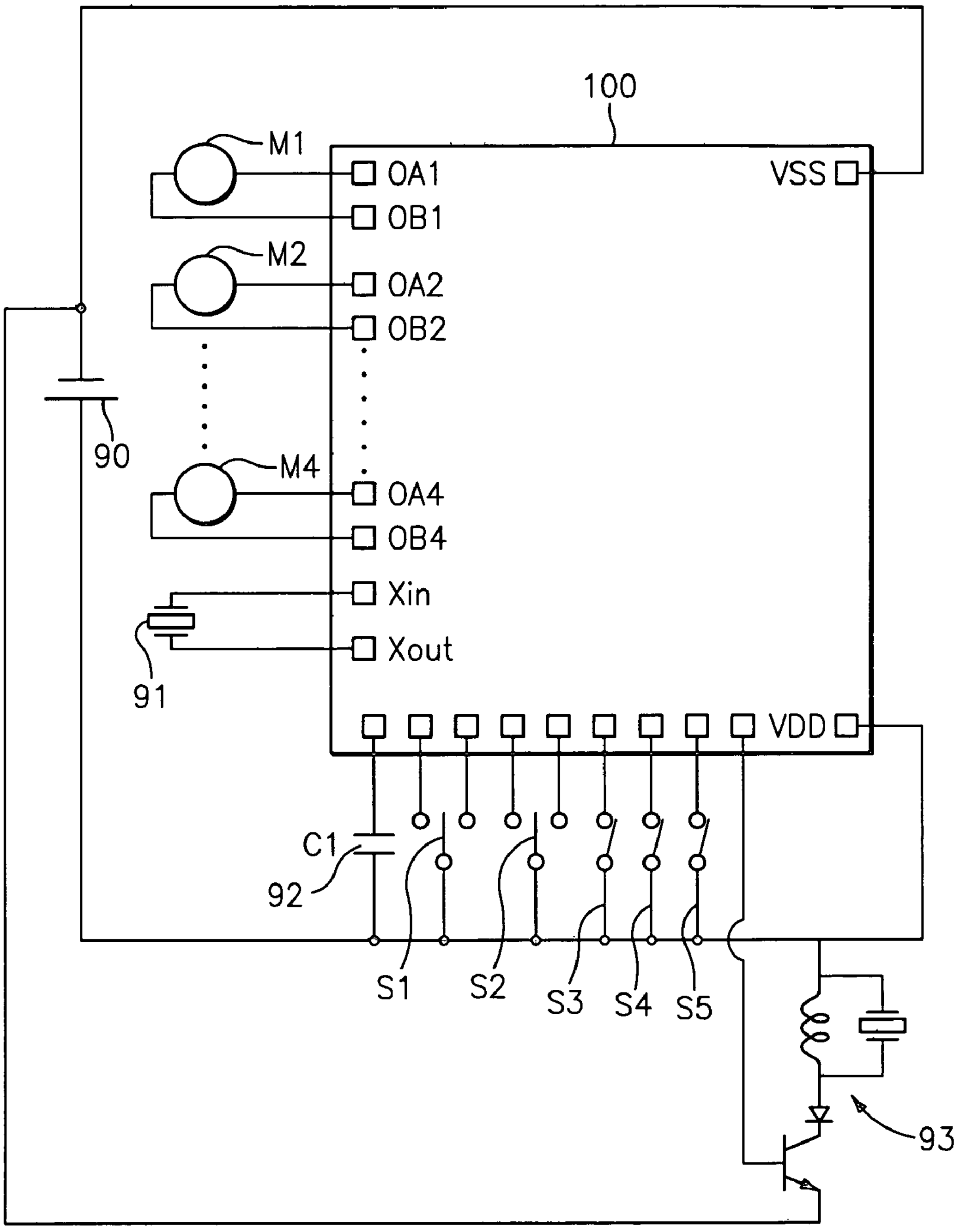
FIG. 3 is a circuit diagram for an electronic device constructed in accordance with the present invention.

Reference is now made to FIG. 3, which illustrates a circuit diagram for a preferred construction of electronic device 10. Generally speaking, controller 100 is preferably an integrated microcontroller typically used with electronic watches which, as will be more particularly disclosed below with reference to FIG. 4, integrates onto a single chip, a CPU core, a motor hand control circuit, an input/output control circuit, addressing and decoding functionality, memory and motor drivers.

As illustrated in FIG. 3, electronic device 10 includes, among other things, a battery 90, a resonator 91 to provide basic timing, a filter capacitor 92 and interface connections to motors M1–M4 and switches S1–S5. A parallel sensor interface is provided for receiving digital signals from a sensor embedded in electronic device 10 and a serial sensor interface is provided for receiving data from a tethered sensor or wireless (remote) sensor, although in any one preferred embodiment, both interfaces are not required. In addition, a well-understood circuit, generally indicated at 93, is provided for alarm activation, and may include among other components a piezoelectric buzzer which may be attached to the back cover of the watchcase.

By way of background, switches S1–S5 are intended to generically indicate both side/top mounted pushers, as well as side mounted rotatable crowns, and thus respond to the actuation (i.e. pulling and/or pushing) action thereof. In the case of crowns, the pulling and or pushing actuations may be provided for setting hands 18, 20 and 21, setting alarm(s) and or actuating backlighting capabilities. In the case of side mounted pushers, start/stop functions, mode selections and calibration of hands 22, 24 and 26 can be effectuated. Of course combinations of the foregoing are within the purview of one skilled in the art. Details of such side pushers or crown actuations/constructions are not material to the present invention, and therefore disclosure thereof is omitted.

Figure 4:
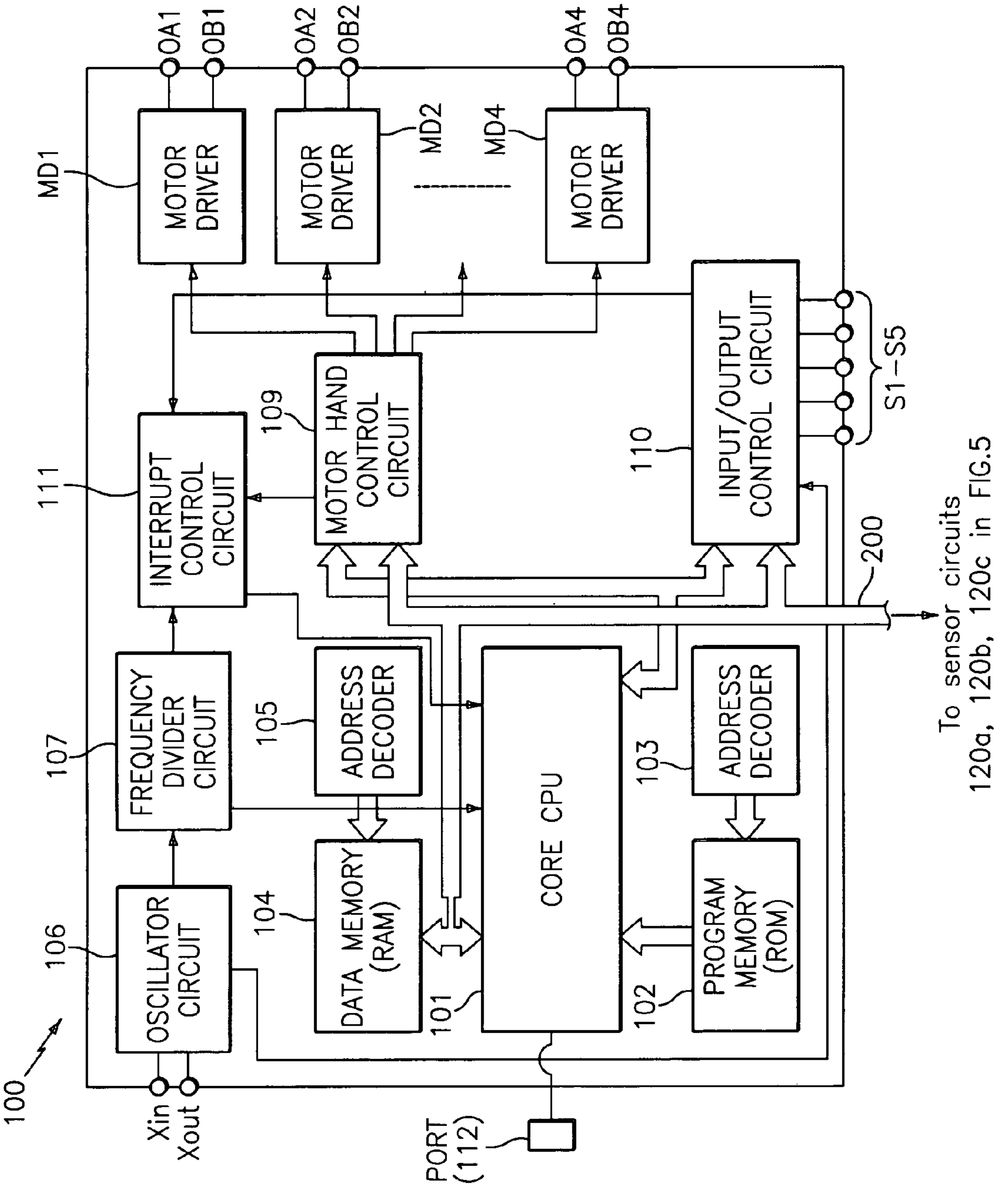
FIG. 4 is a block diagram of a controller, constructed in accordance with the present invention for use in an electronic device constructed in accordance with the present invention.

Reference is now particularly made to FIG. 4 for a description of a preferred construction of controller 100. As illustrated, controller 100 comprises a core CPU 101 which itself comprises an ALU, a calculation register, a stack pointer, an instruction register and an instruction decoder. Controller 100 utilizes a memory mapped I/O bus 200 to communicate with hand control circuit 109, input output control circuit 110 and sensor circuits that will be discussed in further detail below.

A ROM memory block 102 in cooperation with an address encoder 103 provide access to electronic device control software and fixed data. The methodology for the programming for directing CPU 101 on the steps and logic necessary to keep track of and determine subsequent motor positions, as discussed further below, is also coded into ROM 102. Reference may also be made to copending application Ser. No. 10/090,588, the subject matter of which is incorporated by reference as if set forth herein, for a disclosure of a preferred construction for driving and controlling a plurality of stepper motors.

A RAM memory block 104, in cooperation with an address decoder 105, provides storage for intermediate calculation values and also is used to hold current position of the various electronic device hands, such as hands 18, 20, 21, 22, 24 and 26, and to store changeable information such as pill schedules, tide tables, etc., that may be downloaded into controller 100 through a port, generically indicated by 112, which may be an IR port, a keyboard input, a port for optical transmission, LEDs, RF, or through a computer interface, such as that described in U.S. Pat. No. 5,488,571, coowned by the present assigned and incorporated by reference as if fully set forth herein.

Controller 100 includes oscillator circuit 106 which oscillates at a frequency determined by resonator 91, and in the preferred embodiment, this frequency of oscillation is 32768 Hz. A frequency divider circuit 107 divides the output of oscillator circuit 106 to generate appropriate timing signals for timekeeping, motor control and data acquisition functions.

A motor hand control circuit 109 receives a commanded "next number of pulses" from CPU core 101 and generates the pulsed and phased signals necessary to move a desired motor (M1–M4) a desired amount and in a desired direction. Pulse outputs of the motor hand control circuit 109 are buffered by motor drivers MD1–MD4 and applied to motors M1–M4.

An input/output control circuit 110 controls the crown actuations and pushbutton switches of FIG. 3 and provides such signaling information to CPU 101.

An interrupt control circuit 111 is connected to frequency divider circuit 107, motor hand control circuit 109 and input/output control circuit 110, and outputs timer interrupts, motor control interrupts, and key interrupts to CPU 101.

Figure 5:
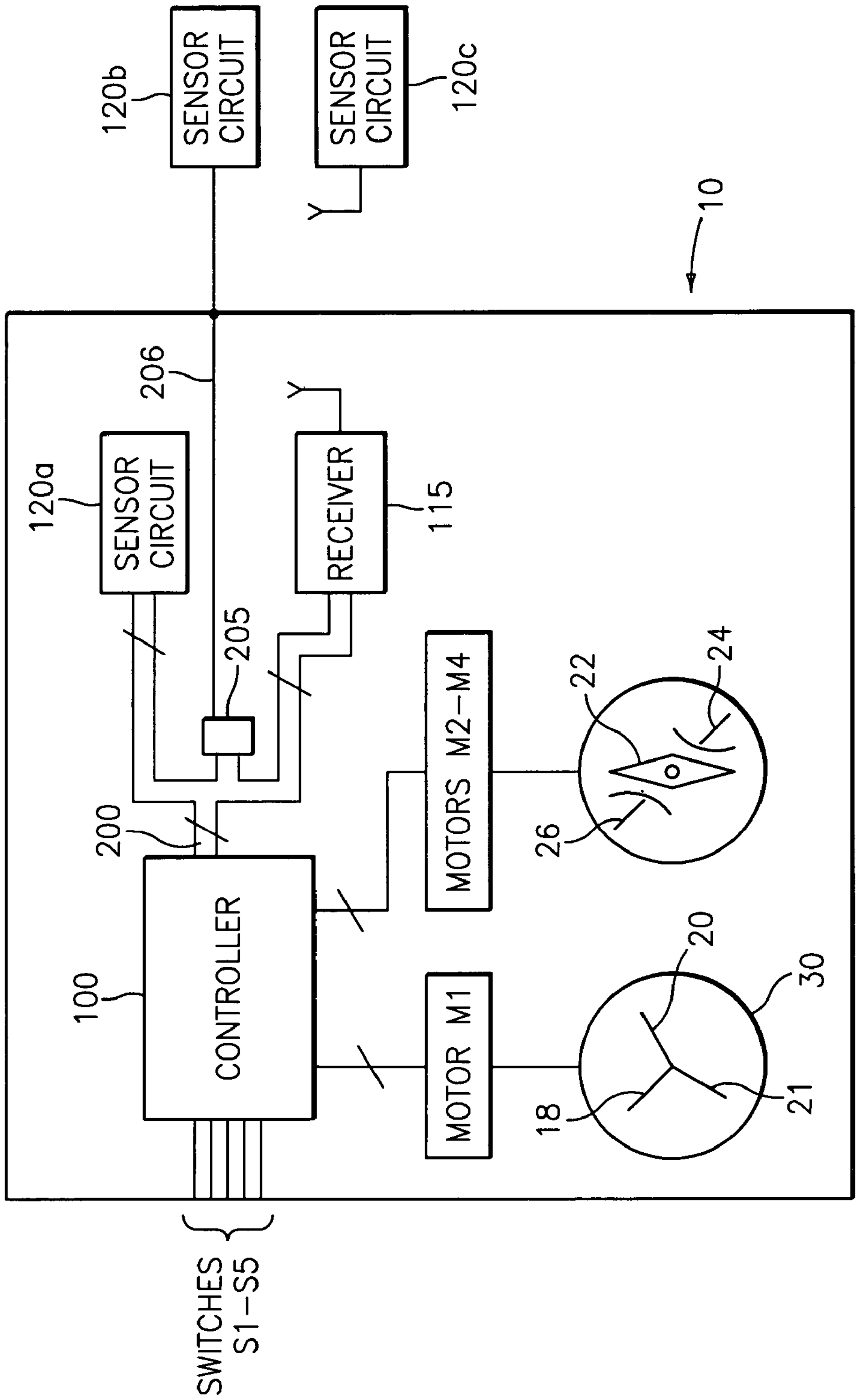
FIG. 5 is a block diagram showing certain other features and construction of an electronic device constructed in accordance with the present invention.

Reference is thus now made to FIG. 5, which is an overall block diagram of the circuitry of electronic device 10 and includes circuit elements to interface electronic device 10 to "the outside world."

In particular and as indicated above, controller 100 directly or indirectly controls the movement of the respective hands to display chronological data, analog representations of data stored in ROM and/or RAM, and analog representations of parameters measured through sensors. In this regard, electronic device 10 may comprise one or more sensor circuits for measuring external parameters, and providing information to be displayed on electronic device 10. Such external parameters include, but are not limited to ambient temperature, altitude, body temperature, heart rate, and compass headings.

Preferred embodiments of the invention may include an embedded sensor circuit 120*a* that is integral with the body of electronic device 10 for measuring altitude or compass headings, for example; a tethered sensor circuit 120*b* that may be electrically connected to electronic device 10 but is remote from the electronic device 10 for measuring parameters such as body temperature or blood pressure, for example; and a remotely located sensor circuit 120*c*, such as in a cheststrap (i.e. a heartrate monitor) that is wirelessly connected through a radio link.

As shown in FIG. 5 sensor circuit 120*a* is "hard wired" through parallel connections to the memory mapped I/O bus 200. Sensor circuit 120*a* is discussed further below but it is noted here that sensor circuit 120*a*, being an altitude sensor circuit in a preferred embodiment, includes an analog portion for sensing a physically measurable value that varies with altitude and an A/D subcircuit with associated preamplification, filtering and sample and hold for converting the measured value into a digital number. The output of the A/D subcircuit, which may be a digital number proportional to the measured value, is applied directly to memory mapped I/O bus 200.

On the other hand, sensor circuit 120*b*, which in the preferred embodiment is a body temperature sensor, also includes an analog portion and an A/D subcircuit with associated preamplification, filtering and sample and hold for converting the analog measured value into a digital number. For sensor circuit 120*b* however, the invention preferably uses a serial link to connect sensor circuit 120*b* and electronic device 10, so that in addition to the A/D portion which has a parallel output format, a parallel to serial converter portion is preferably used and a UART 205 is used to convert back to parallel format for application to the memory mapped I/O bus 200.

Lastly, sensor circuit 120*c* may be a heartrate monitor and is wirelessly connected to electronic device 10. In addition to a basic heartrate sensor, sensor circuit 120*c* includes a radio transmitter for sending data to an RF receiver 115 in electronic device 10. The output of receiver 115 is thus also connected to the memory mapped I/O bus 200.

We note that in alternate embodiments a delta sigma type A/D converter may be used to simplify the processing of the generally low-level sensor signals.

It should be noted that although FIG. 5 depicts a highly integrated design wherein all timing and display functionality is controlled in controller 100, alternate embodiments could separate the timekeeping functions from those processing and displaying stored or sensed data. For example, hands 18, 20 and 21 may be controlled by controller 100 or through a timekeeping section, while hands 22, 24 and 26 are controlled by controller 100 based on data stored in the data memory and/or information received from one or more sensor circuits.

4. Hand Control

All of the foregoing makes clear that in an embodiment that may not utilize sensors to measure external parameters, controller 100 will have in its memory (or will be able to receive from an external source (such as via a telephone link, computer link, wirelessly, or the like) for storage in such memory) all the necessary data representative of the stored information such as tide or "pill-taking" information, by way of example, and in an electronic device that comprises one or more sensors, controller 100 will receive the necessary data representative of the measured parameter(s) via one or more of sensor circuits 120*a*, 120*b* and/or 120*c*.

As noted, analog hands 18, 20 and 21 are preferably used to indicate time and hands 22, 24 and 26 are preferably used to display either values stored in ROM 102, values stored in RAM 104 or current data collected by sensors 120*a*, 120*b* or 120*c*. Since the display of time information using stepper motors is known to one skilled in the art, the following discussion will address display of stored information and "live" information collected from sensors 120*a*, 120*b* and 120*c*.

Advantageously, and as is also known to those skilled in the art, a stepper motor will remain in its last position unless pulsed to move. Therefore to smoothly display continuously varying information with an analog hand driven by a stepper motor, the preferred embodiment delivers to the stepper motor the necessary number of pulses to move the rotor of the stepper motor between a desired position at t=0, for example, and a position desired after some small time interval later.

As indicated above, the preferred embodiment will utilize sensors with A/D conversion to facilitate computation and interface to the memory mapped I/O. Therefore to determine the number of pulses and direction to move a rotor of a stepper motor to its next position it is necessary to know where the rotor is in terms of a number of pulses, subtract that from the new sensor value converted to pulses, and based on the magnitude and sign of the difference, pulse the stepper motor the number of pulses needed to move the rotor the desired amount and in the desired direction.

In an alternate embodiment the calculations above can be performed using converted sensor values in digital format and then by applying the appropriate scale factors, develop the number of pulse determined above.

More specifically, in the case of an embedded sensor 120*a* that measures altitude, altitude values are expected to change slowly so that in the preferred embodiment an interval of for example, 10 seconds, may be appropriate. Clearly, selection and implementation of smaller or larger time intervals between sampling is well within the knowledge of one skilled in the art. In this example, if the electronic device is not moving the altitude is not changing, the subsequent subtraction of current altitude values (or a signal proportional to the value) from a next value calculated in controller 100 gives a result of zero, which is sent to motor hand control circuit 109 so that the respective stepper motor is not pulsed to move.

On the other hand, if a value calculated in controller 100 by subtracting a new A/D conversion value (or signal proportional thereof) is greater than the resultant value determined at the previous A/D conversion step, controller 100 will signal motor hand control circuit 109 to step the respective stepper motor a predetermined number of steps in a direction to indicate an increased value (if the new measurement is greater than the previous measurement) or in the opposite direction if the new measurement is less than the previous measurement.

Each sensor sample may require an A/D conversion to take place. Well-known programming techniques then require the controller to determine whether the resultant value from each subsequent A/D conversion is greater than, less than or equal to the resultant value determined at the previous A/D conversion step. In the case where the resultant values are equal, the controller will not signal motor hand control circuit 109 to step the respective stepper motor and control of the routine will pass back for another sensor sample. On the other hand, if the resultant value from this subsequent A/D conversion is greater than the resultant value determined at the previous A/D conversion step, controller 100 will signal motor hand control circuit 109 to step the respective stepper motor a predetermined number of steps, in one of a clockwise or counterclockwise direction, representative of the increase in the resultant values. A similar (albeit in the opposite direction) procedure occurs in the event that the subsequent resultant value is less than the resultant value from the previous A/D conversion step.

Although the preferred construction is the use of stepper motors as disclosed herein, it should be understood that the present application is not so limited. For example, other types of actuation mechanisms, may be used in place of the stepper motors disclosed herein, while still remaining within the scope of the present invention.

Accordingly, in these embodiments, it should be understood that an actuation mechanism would be operatively coupled to the controller and would rotate the at least one display hand in at least one of a clockwise and counterclockwise direction in predefined increments.

5. Sensors a. Altitude or Compass

As noted, in a preferred embodiment, sensor circuit 120*a* may measure altitude or compass headings. Such a sensor circuit may be disposed within module 15, or may be physically coupled thereto, as illustrated in FIG. 6, with a covering 2 to protect it.

Figure 7:
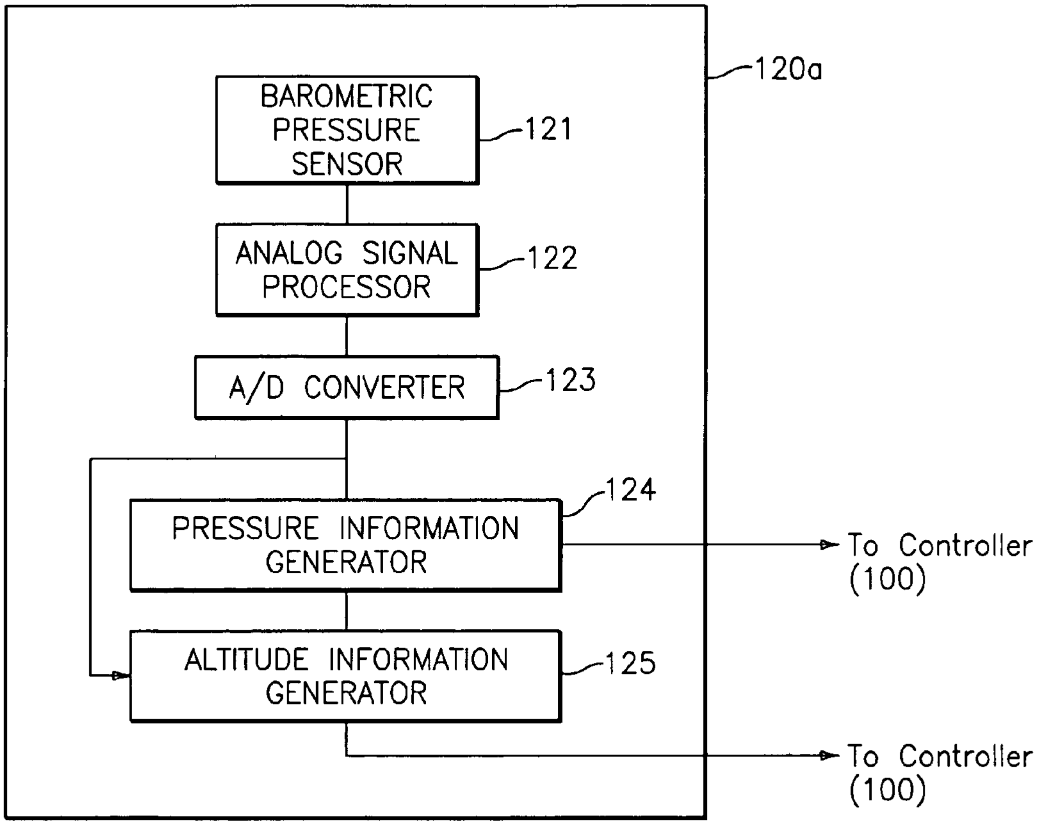
FIG. 7 is a block diagram of a sensor circuit for measuring an external parameter, such as altitude and/or barometric pressure.

The basic construction of an altitude sensor circuit 120*a* for measuring altitude and/or barometric pressure is shown generally as a block diagram in FIG. 7, and described more fully in U.S. Pat. No. 5,224,059, the subject matter of which pertaining to the configuration of the sensor circuits is incorporated by reference as if fully set forth herein. By way of general description, circuit 120*a* comprises a barometric pressure sensor 121, an analog signal processor 122 for processing the output signal from pressure sensor 121, an analog to digital converter 123 for converting the output signal from the analog signal processing circuit to a digital signal, a barometric pressure information generator 124 for generating barometric pressure information based on the output signal from the analog to digital converter and an altitude information generator 125 for generating altitude information based on the output signal from the analog digital converter.

Figure 10:
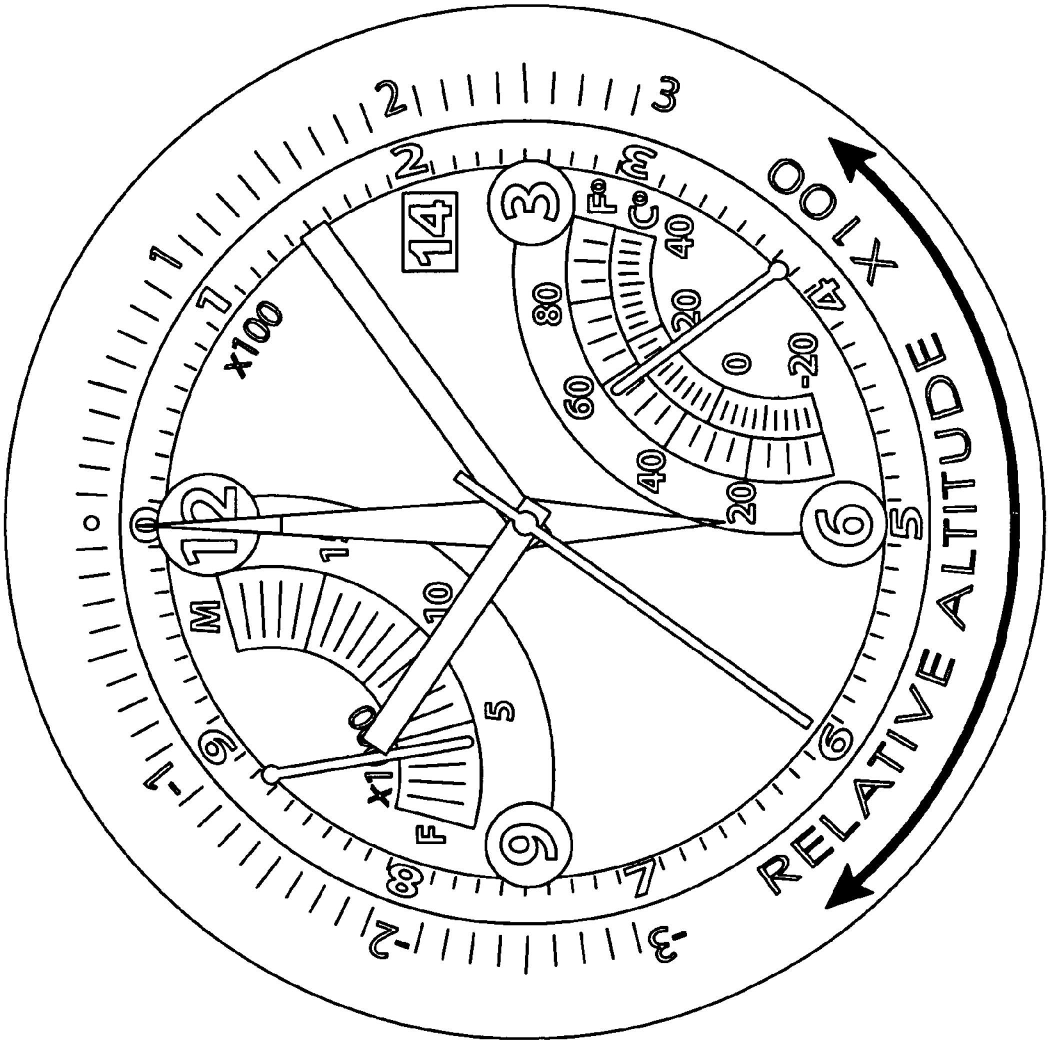
FIG. 10 is a top plan view of yet another electronic device constructed in accordance with a specific embodiment of the present invention.

In the present invention and as illustrated in FIG. 10, barometric pressure information is not displayed, but as will be apparent from the ensuing description, the present invention contemplates that both pressure and altitude information are displayable, either simultaneously, individually, or alternatively, as desired.

As would be well-known to those skilled in the art, altitude information generator 125 preferably comprises circuitry, such as a temperature compensating circuit and compensating circuit for processing and compensating the altitude information, as well as memory for storing calendar information, temperature coefficients, a sea level temperature processing circuit for generating compensation data, and memory for storing and providing regional information such as latitude information and altitude compensation data. Likewise, such a circuit may be distributed, such that ROM 102 or RAM 104 stores the needed data.

As alluded to above, the pressure measured by the pressure sensor in the pressure sensor unit is converted by the A/D converter 123 into a value representing the pressure.

Altitude information generator 125 serves as a processor for calculating an altitude at the standard atmosphere and converting the value of the pressure converted by A/D converter 123 into an altitude assuming the standard atmosphere and utilizing well-known algorithms, such as those described in U.S. Pat. No. 5,224,059. Memory is provided for storing regional information for processing the temperature at sea level at a certain place and at a certain month, since temperature coefficients of the temperature at sea level in accordance with month and area as regional information are needed for accurate calculations.

If barometric pressure is also to be displayed, pressure information generator 124 is additionally provided. Here a pressure variation information generator circuit may be provided for generating information relating to variations in pressure based on the information data output from the pressure information generator 124. Generally speaking, the barometric pressure sensor would provide a barometric pressure signal proportional to a barometric pressure which converts the obtained pressure into an electrical signal utilizing a pressure sensor. Here again, A/D converter 123 would convert the signal from a sample-and-hold circuit and output the signal as converted data, while a pressure information generator would process the converted data output from A/D converter 123, to convert the data into sensor information data, i.e., pressure information.

The actual pressure sensor may be any kind of conventional pressure sensor, well-known in the art.

b. Temperature or Blood Pressure

Instead of a sensor circuit being provided within module 15, the sensor circuit may also be essentially tethered to module 15 and indicated schematically as sensor circuit 120*b*, such as that described in U.S. Pat. Nos. 6,314,058 or 4,407,295, the subject matter of which pertaining to the construction and coupling of the sensors to the module being incorporated by reference as if fully set forth herein. Here, the signal produced by the sensor may likewise be fed into a modulator and converted into a digital signal utilizing an A/D converter as disclosed above, and would now be understood from a reading of the present disclosure.

Using such a tethered sensor circuit 120*b*, parameters such as body temperature, heart rate, blood pressure, or other physiological parameters using noninvasive techniques can be measured, including lung capacity, through the use of a remote sensor containing a piezo-resistive element or a thermistor. The sensor could then be placed either in the mouth or in the nose and the duration of expulsion of air could be measured and displayed in accordance with the present invention. In each of the foregoing examples, the sensor circuit contains the appropriate circuitry, as implemented through employment of microelectronics, to take the sensed parameter and convert it into an information signal which is relayed through connector 206 (FIG. 5) into electronic device 10 for subsequent processing and display.

c. Remote Sensor (Wireless)

As illustrated in FIG. 5, sensor circuit 120*c* may be remotely located from electronic device 10, such as in a chest strap, and in the preferred embodiment, the parameter being measured is a person's heartrate. Wireless transmission may be over one or more frequency ranges, although the transmitter of the chest unit is preferably frequency matched to the receiver in the wrist unit so that the digital signal wirelessly transmitted from the chest unit 12 will be received by the wrist unit 14. In a preferred embodiment, the wireless transmission is an RF signal.

It is within the discretion of the designer to decide what information gets processed in the transmitter and what information gets processed in the receiver (i.e. electronic device 10). For example, in a preferred embodiment, the conversion of an ECG signal from a heartbeat to a digitized signal in the form of a digital number representative of the heart rate is computed in sensor circuit 120*c*, and then transmitted to complementary receiver 115. Alternatively, the digital number representative of the heart rate may be calculated in the electronic device 10.

The signal being transmitted from the chest strap can represent a full heartbeat rate, or just a portion of it, for example, the number of ECG pulses in a multi-second interval can be represented and multiplied by the appropriate scaling factor (i.e. a 10 second interval is then multiplied by 6). Again, the calculations can be done in electronic device 10 or in the transmitter unit (i.e. sensor circuit 120*c*) if the full heartbeat rate is to be transmitted to receiver 115. In a preferred embodiment, the digital signal representing the person's heartbeat is received and displayed by one or more display hands, and in the preferred embodiment, hand 22 (See FIGS. 9A, B).

One skilled in the art would clearly be able to design an appropriate transmission protocol for acquiring and processing data from the transmitter to the electronic device for subsequent display, and therefore, details thereof will be omitted for purposes of brevity.

It should be understood that the foregoing measurement of heart rate is by way of example and not limitation, as it should be readily appreciated by those of skill in the art that a signal indicative of other physical conditions could be monitored. For example, an acoustical sensor can detect a pulse or a thermometer sensor can detect a temperature. It can also be seen that such parameters such as heartrate, as but one example, can also be measured with the appropriately configured sensor circuits 120*a* and 120*b*.

6. EXAMPLES

With the foregoing having provided a disclosure on how parameters are measured and how representative data (stored or measured), is inputted to controller 100 for communicating with motor hand control circuit 109 to cause the appropriate degree and direction of rotation of the rotors for stepper motors M2–M4, reference is now made to the remaining figures and disclosure for an understanding of certain preferred specific embodiments of the present invention. It should also be understood that all the following figures only illustrate the necessary features and construction that distinguish them from other specific embodiments disclosed herein. That is, FIGS. 8–11 do not illustrate entire electronic devices, but rather only customized dials and features thereof to construct the present invention and appreciate the versatility thereof. But in the interest of caution, it should be understood that the features and advantages of the invention that will hereinafter be disclosed are preferably incorporated into an electronic device, such as that disclosed and illustrated in FIGS. 1 and 6.

a. Microcontroller Based

Reference is thus made first to FIGS. 8A–8D in connection with the following for a disclosure of a specific preferred embodiment of the present invention. Generally speaking, this first specific embodiment is one that needs not rely on the use of sensors to provide information regarding external parameters, and displays information, in an easily readable manner, that has been previously stored in controller 100, and it should be reemphasized that the present disclosure provides the platform by which any number of informational parameters can be displayed by electronic device 10.

Figure 8A:
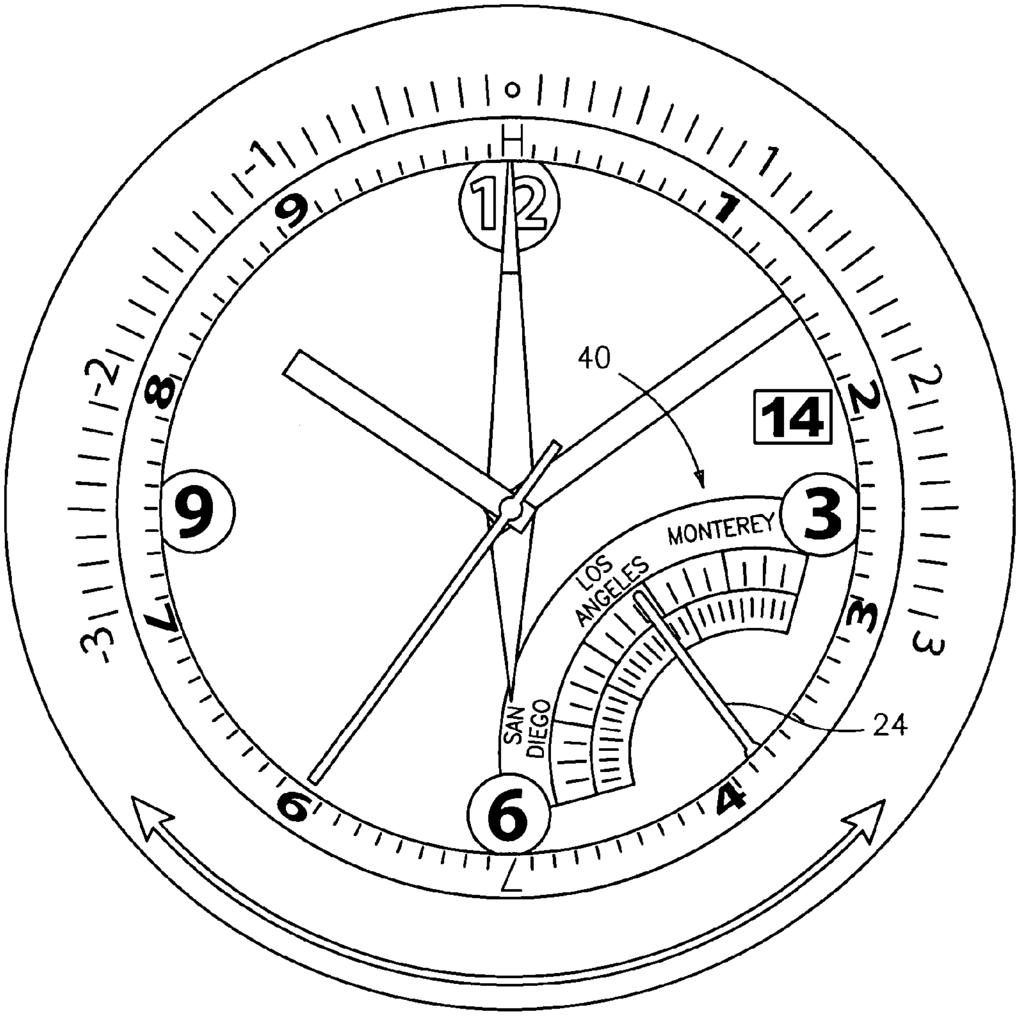
FIGS. 8A–8D are top plan views of electronic devices constructed in accordance with specific embodiments of the present invention.

For example, FIG. 8A illustrates an electronic device for displaying tide information along the California coast, such as whether the tide is high or low, and the geographic location pertaining thereto. In particular, hand 22 may be used to display the height of the tide, while one of the display areas is used (here by example, display area 40) to display various locations pertaining thereto. Hand 24 will point to the particular location. Moon phases or other related information could also be simultaneously displayed (such as on display 50, not shown in this figure). One or more pushers S1–S5 may be used to cycle through various locations so that with each successive actuation of the pusher, hand 24 moves one position to point to a different location, with hand 22 thus working in connection to indicate the tide at that different location. One skilled in the art would clearly know how to program controller 100 to receive the pusher actuations and change the positioning of hand 24, at least based in part on the foregoing disclosure regarding hand movement. If display 40 incorporates the advantages of FIG. 8D (discussed below), pusher actuations could actually be used to change the displays so that a user could view any desired location merely by scrolling through a set of geographic locations. U.S. Pat. No. 5,299,126 describes an embodiment wherein memory stores the applicable table of tide times, heights and geographic offsets, which would be helpful in constructing a tide watch that utilizes the features and construction of the present invention.

Figure 8B:
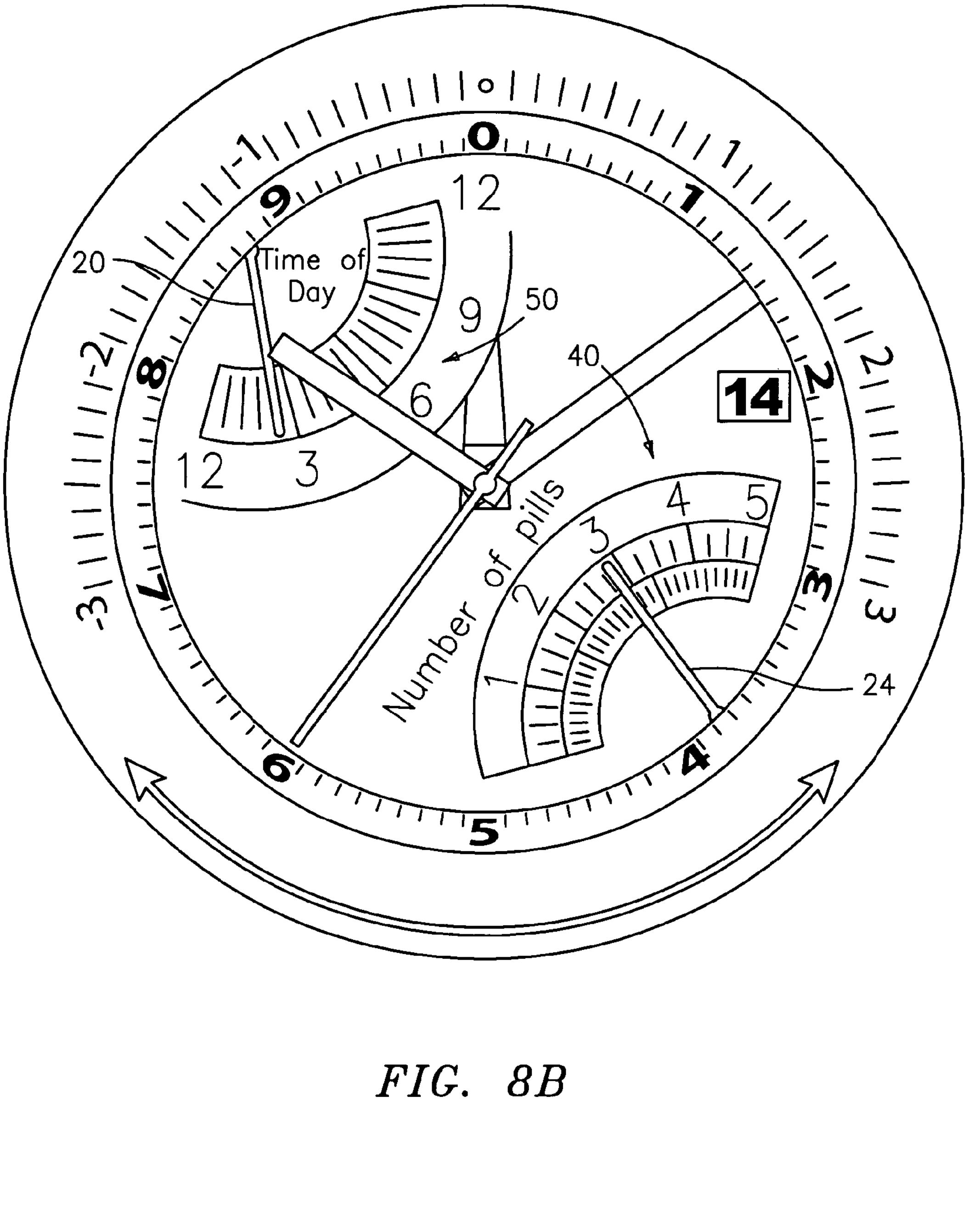

On the other hand, FIG. 8B illustrates an electronic device display for displaying medical information, such as when medicine should be taken, and how many pills at each time interval. Here for example, hand 26 may be used to display time intervals (12 o'clock, 3 o'clock, 6 o'clock, 9 o'clock, 12 o'clock) with hand 24 being used to display the number of pills (1–5) to be taken at each interval.

Figure 8C:
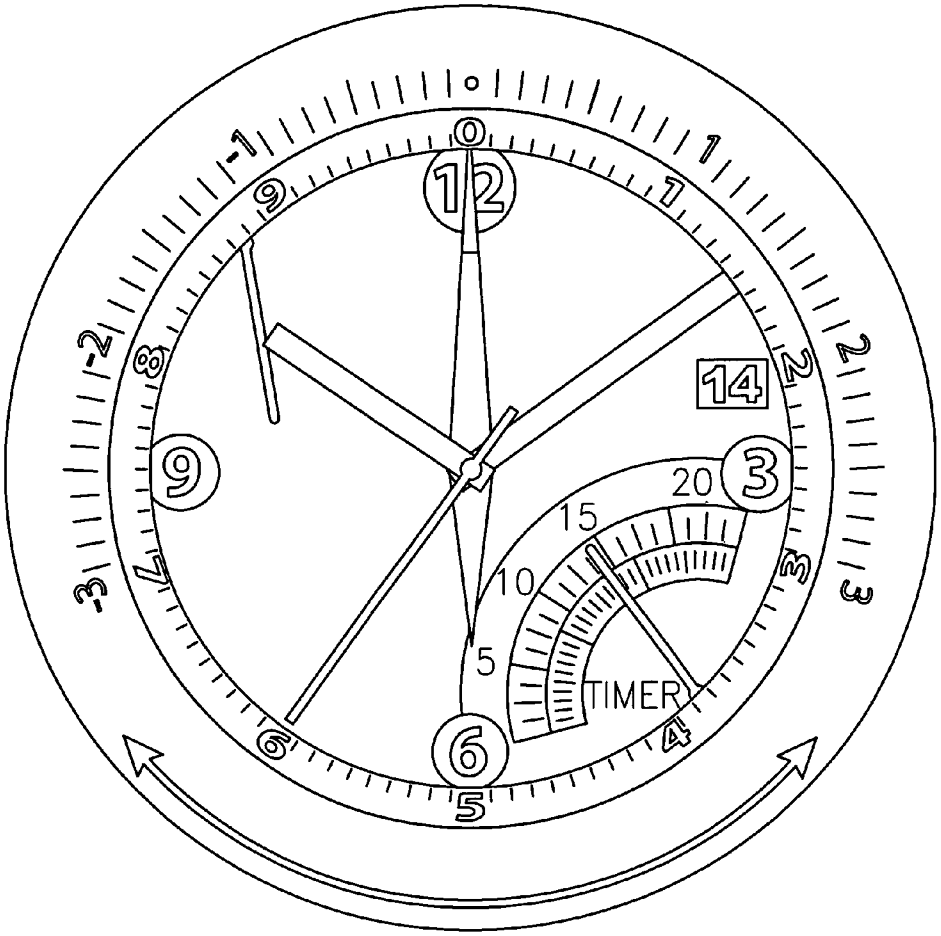

Similarly, FIG. 8C illustrates the use of display 40 being used as a count-down timer, with hand 24 being used to display the number of minutes left. In connection with this FIG. 8C, electronic device controller 100 would be appropriately programmed to permit a user to set the desired number of minutes for the countdown timer. Again, such information could be inputted through the use of a side pusher. The number of actuations of the side pusher would cause controller 100 to cause motor hand control circuit 109 to step the appropriate rotor, here the rotor for motor M3, the proper number of steps to indicate an additional minute was selected for the countdown timer. Clearly, a different pusher could be used to decrement the timer display in a similar manner.

Another contemplated advantageous feature is that hand 24 may oscillate at some frequency, such as 1 Hz, when operating in the countdown timer mode to allow the user to know that the electronic device is actually in the countdown timer mode. Such a feature would be implemented by rotating the rotor of stepper motor M3 the appropriate number of pulses in the forward and reverse direction at the desired frequency while the timer is operational, all the while ensuring that controller 100 maintain information on the rotor position so that the proper rotation of the rotor can be effectuated after each minute of elapsed time.

The use of the foregoing constructions and arrangements to display tide/moon information, pill taking and timers should be considered exemplary and not in a limiting sense, as one skilled in the art should be able to envision many other advantageous uses of the present invention, all while remaining within the scope of the claims.

Figure 8D:
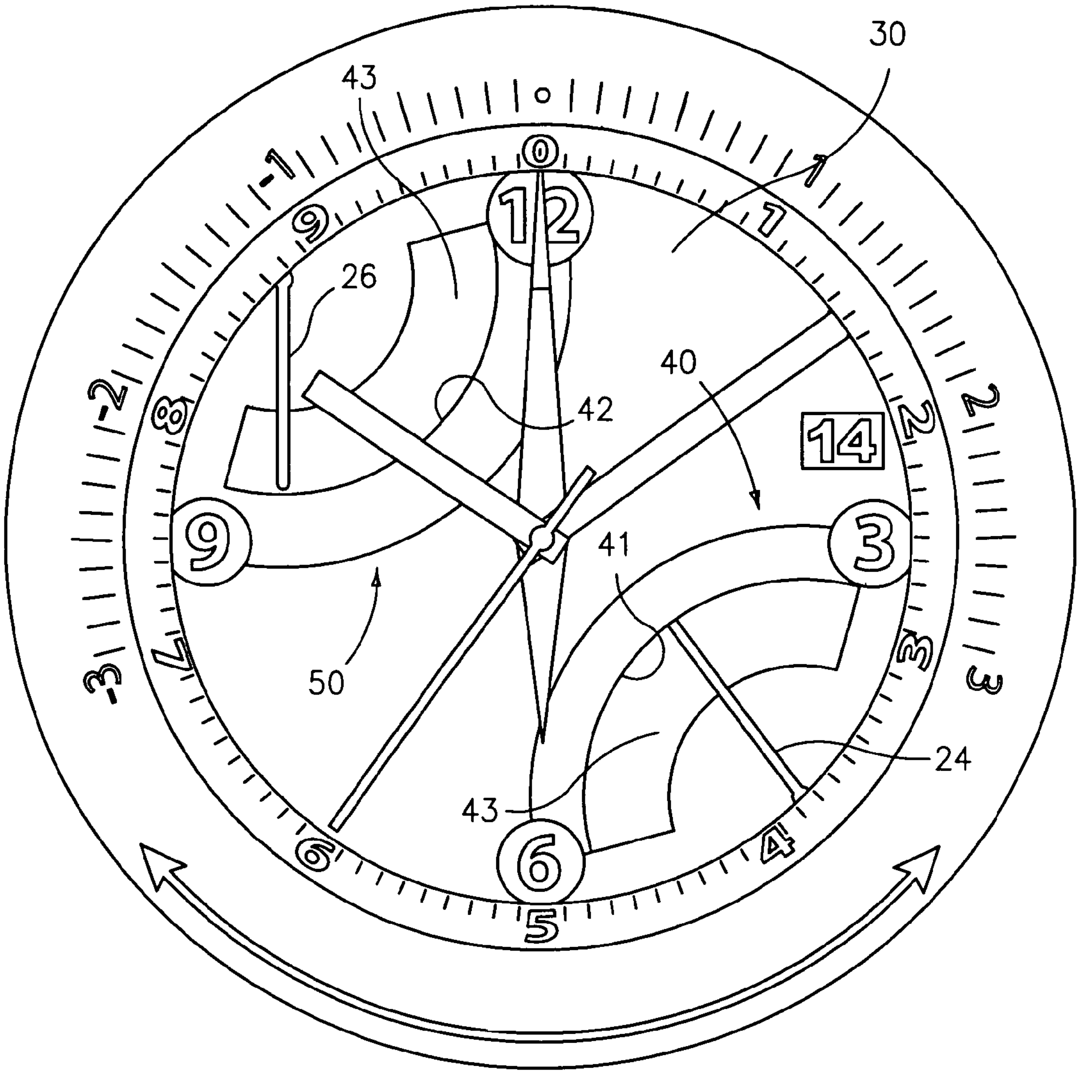

In accordance with a modification of the present invention, another feature of the invention is illustrated in FIG. 8D wherein dial 30 is provided with windows 41 and 42, respectively in display areas 40 and 50. In this specific embodiment, one or more LCD panels, generally indicated at 43, are provided behind dial 30 and aligned with the respective windows 41, 42. The use of such an LCD window is quite old in the art, and incorporated within watches coined "combo" watches. An exemplary construction of such an "analog/digital" or "combo" watch is described in U.S. Pat. No. 5,691,962, coowned by the present assignee and incorporated by reference as if fully set forth herein.

In this embodiment of FIG. 8D, the LCD display can display various scales that are particular to the desired displayable information. In this way, a single electronic device can be manufactured with all of the aforementioned modes being selectively displayable on one display and in one electronic device. Additionally, the mode can easily be displayed in the windows 41 and/or 42 of the dial 30, thus allowing the user an ability to see the modes through which he/she is cycling. In a similar manner, the scales for a single mode can vary as well, since one skilled in the art would know how to excite the appropriate LCD crystals to have a scale, grid or other measuring design appear on the LCD panels 43. Controller 100, knowing the mode, the scale appearing on LCD panels 43, and the position of the rotors for motors M3 and/or M4, could coordinate the display such that any mode could be displayed by the use of differing displayable scales. As alluded to above, in the embodiment illustrated in FIG. 8A, a user could selectively cycle through a plurality of cities/locations for display in window 41 since the city names that would appear in window 43 of display 40 would change with each actuation of a side pusher, for example.

Accordingly, it can be seen that the foregoing examples illustrate and disclose embodiments wherein the wearable electronic device, which may be an electronic timepiece, such as a watch, may include at least an hour hand and a minute hand for conveying time of day information and rotatable about an at least essentially center axis and at least one display hand rotatable about an axis other than the center axis and positioned on the dial side of the dial. The actuation mechanism, being a stepper motor by way of example and not limitation, rotates the at least one display hand in at least one of a clockwise and counterclockwise direction in predefined increments. The controller is operatively coupled to the actuation mechanism and causes the actuation mechanism to rotate the at least one display hand in at least one of the clockwise and counterclockwise direction in the predefined increments based at least in part on data stored in the controller, wherein the positioning of the display hand as it rotates in the one of the clockwise and counterclockwise directions in the predefined increments conveys information relating to the stored data.

In the embodiments disclosed, the rotation of the display hand by the actuation mechanism (such as the stepper motor) is not dependent of the time of day, and thus, is patentably distinguishable from a chronograph display and biorhythmic displays. More specifically, the rotation of the display hand is not dependent on the rotation of the hour or minute hands, and thus the actuation mechanism can rotate the display hand independent of the time of day. Again, with the actuation mechanism of the display hands 24, 26 not being mechanically coupled to the movement of the hour and minute hands as in the prior art, significant restraints upon the limitations of what can be displayed on the dial are removed, as disclosed above. That is, while the hour and minute hands are coupled to a gearing arrangement, the actuation mechanism can rotate the display hands (i.e. hands 24 or 26) independently of any rotation of the hour and minute hand. For completeness, it should now be seen that in the preferred embodiment, the actuation mechanism comprises a stepper motor that itself comprises a rotor, the stepper motor operatively coupled to the controller, for stepping in at least one of a clockwise and counterclockwise direction in the predefined increments. Preferably, the stepper motors are bi-directional.

It should be appreciated that utilizing a receiver and memory in the controller, such as that disclosed above, the wearable electronic device or timepiece of these microcontroller driven embodiments can receive and store the data from an external source, and thereafter, can convey information relating to the stored data in the analog manner as disclosed above.

With reference to the embodiment of FIG. 8D, it should be appreciated that the present invention provides a unique multimode electronic device. Here, the controller is operable in a first mode and at least a second mode and the display is viewable through the at least one window in the dial, wherein the display displays informational indicia corresponding to the mode in which the electronic device is operating, and wherein the informational indicia is changeable based on the mode in which the wearable electronic device is operating; wherein the positioning of the display hand as it rotates in the one of the clockwise and counterclockwise directions in the predefined increments conveys the information and wherein the controller operatively controls the positioning of the hand so that the hand can display the information in the analog manner for each of the at least two modes. In a specific embodiment, the display hand is rotatable about an axis other than the center axis of the dial. Although preferred, it is not required that the display be an LCD display.

b. Sensor Illustrations

Figure 9A:
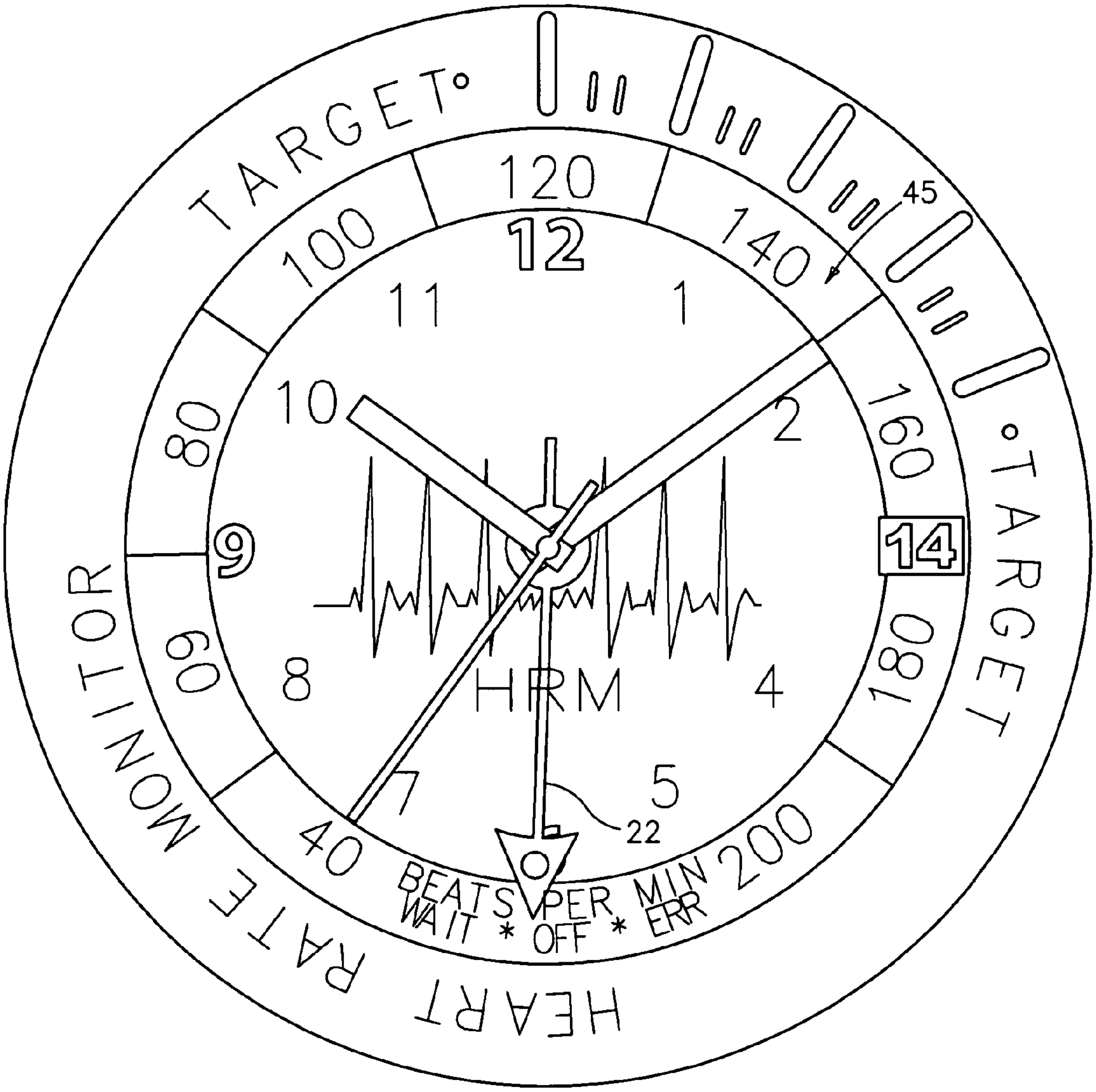
FIGS. 9A–9B are top plan views of electronic devices constructed in accordance with other specific embodiments of the present invention.
Figure 9B:
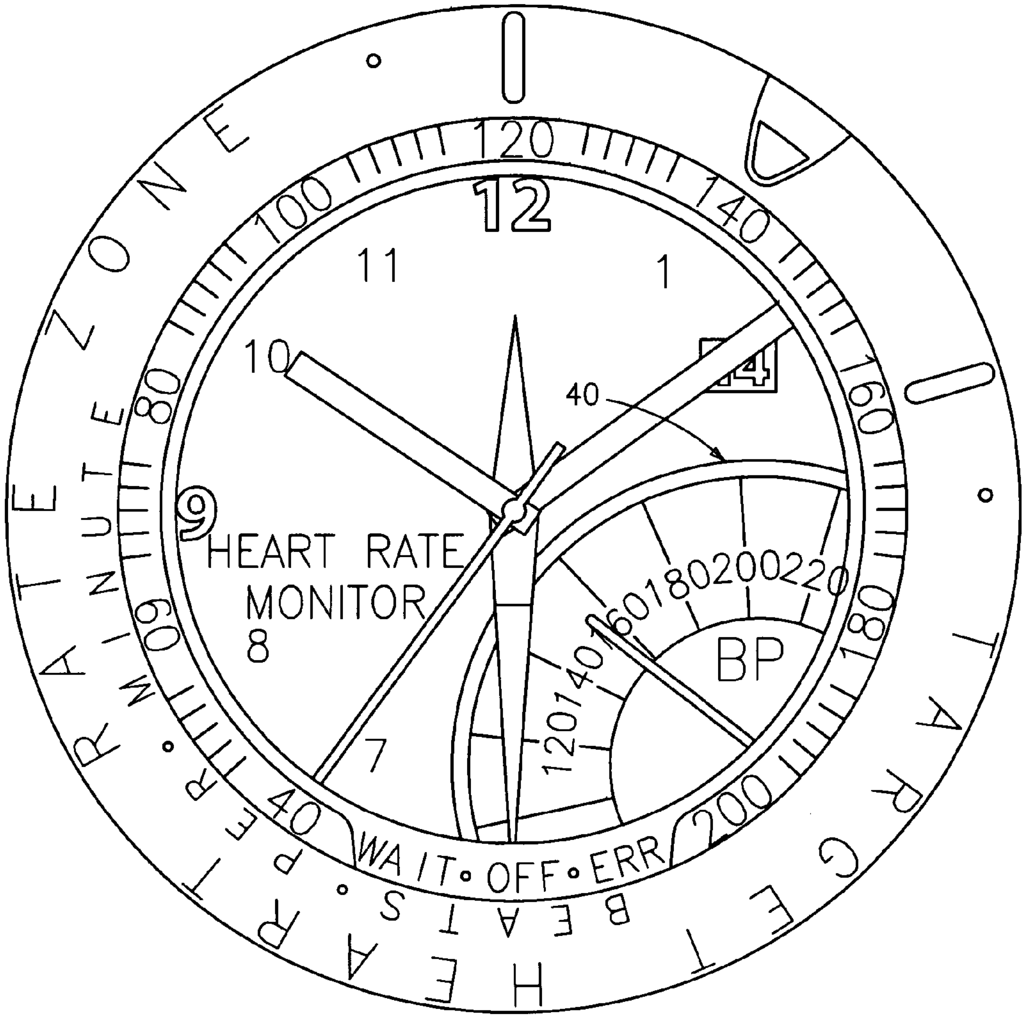

Reference is now made to FIGS. 9A–9B in connection with the following for a disclosure of another specific preferred embodiment of the present invention. Generally speaking, this next specific embodiment is one that incorporates the use of one or more sensors disclosed above, and it should now be understood that the measurement of heartrate, for example, can be accomplished with sensor circuit **120*b* or sensor circuit 120*c***.

In FIG. 9A, hand 22 may be used to rotate and point to the particular heart rate of the user, as the display, generally indicated by 45, shows a scale of heart rates ranging from 40 beats/min. to 200 beats/min. Still further, FIG. 9B illustrates an electronic device display also for displaying heartrate information as in FIG. 9A, although this FIG. 9B additionally illustrates the capability of displaying additional information, such as blood pressure, with the use of display 40, and hand 24, in particular. In the particular embodiment, the systolic pressure is displayable. However, using the inventive feature noted above, namely, providing windows 41 and/or 42 with an LCD panel 43 therebehind, other related parameters, such as the diastolic measurement, is also selectively displayable (again using pushbuttons and easily programming methodologies for changing the display scales and measurements). In a similar manner, display 40 may be a countdown timer, or selectable between a countdown timer and a blood pressure display. Clearly, a separate countdown timer could be added to FIG. 9B in display 50, thus taking advantages of at least two embodiments disclosed herein.

FIG. 10 on the other hand, illustrates a dial 30 particularly configured for displaying altitude and air temperature information. Here, the preferred configuration is to have hand 22 and hand 26 work together to illustrate altitude, with display 45 displaying a ×100 scale and display 50 using an ×1000 scale, all the while hand 24 displays temperature in both degrees Fahrenheit and Celsius. In this embodiment, multiple sensors would preferably be needed. Another U.S. patent that describes a device for measuring altitude and barometric pressure is described in U.S. Pat. No. 5,224,059, the subject matter regarding the measuring of altitudes and barometric pressure being incorporated by reference as if fully set forth herein.

Here again, with the incorporation of LCD panels 43 and one or more of sensor circuits **120*a* and 120*b*, the scales of the displays could vary based on the sensed parameter readings, i.e. the higher one goes, the scales change to provide the user with a more accurate hand indication. In a divers watch for example, the scale of depth on a panel 43** in a display window could vary from 1–10 feet, to 1–100 feet, to 1–1000 feet, as the sensor recognizes that the diver is increasing his/her depth.

Figure 11:
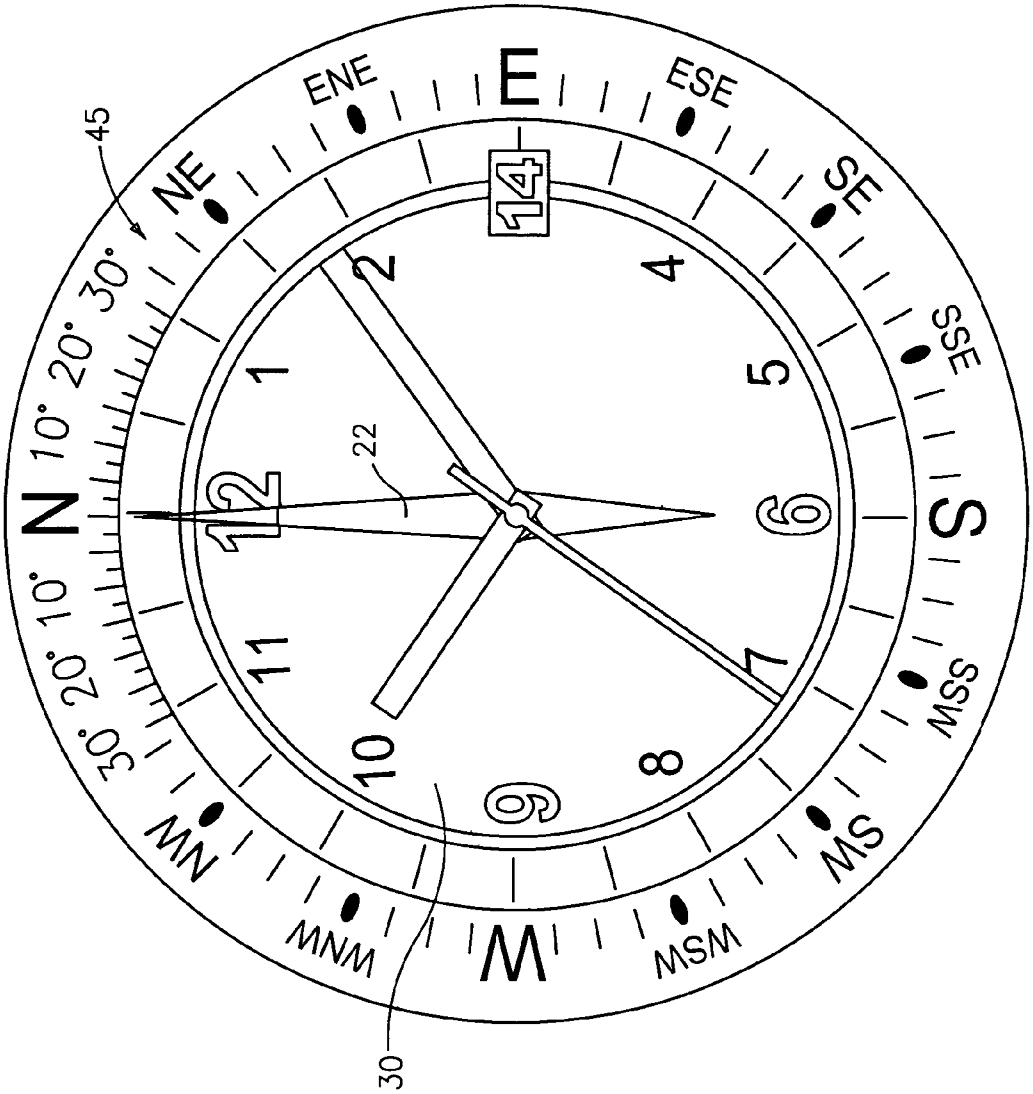
FIG. 11 is yet another top plan view of an electronic device constructed in accordance with still a further specific embodiment of the present invention.

Lastly, FIG. 11 illustrates a dial particularly configured for displaying direction headings (i.e. a compass watch), with display 45 having directional indicia thereon. In this specific embodiment, electronic device 10 will preferably include a sensor circuit 120*a* that is positioned in or coupled to module 15. Directional information will be received by controller 100, and through motor hand control circuit 109, hand 22 will rotate accordingly based on the pulsing scheme provided by controller 100 to circuit 109, as in the manner disclosed above.

The foregoing embodiments illustrate and disclose a wearable electronic device, such as an electronic timepiece that conveys information in an analog manner. Certain of the foregoing embodiments include various combinations of features, such as at least one display hand that is rotatable about an axis other than the center axis and positioned on the dial side of the dial; at least one sensor for sensing at least one parameter external to the electronic timepiece; a controller, operatively coupled to the sensor, for receiving and processing information based on the at least one parameter sensed by the at least one sensor; an actuation mechanism, operatively coupled to the controller, for rotating the at least one display hand in at least one of a clockwise and counterclockwise direction in predefined increments, wherein the increments and direction of the rotation of the at least one display hand are based at least in part on the at least one parameter being sensed by the sensor; wherein the positioning of the display hand as it rotates in the one of the clockwise and counterclockwise directions in predefined increments conveys information relating to the at least one parameter being sensed.

Another convenient way to express the location of the display hand, such as hand 24 or 26 is to consider that the display hand has a first end and a second end, wherein the first end of the display hand rotates about a pivot point spaced apart from a center point of the dial by a fixed distance, and the second end of the display hand sweeps across a portion of the dial side of the dial, wherein the display hand can sweep about an arc, wherein the display hand has a length from the pivot point that is one of (a) shorter than the fixed distance and (b) longer than the fixed distance.

Here again, it should be pointed out that the preferred (but not the required) embodiment is the use of a stepper motor as disclosed above.

If the particular embodiment is a watch, the wearable electronic device may include at least an hour hand and a minute hand for conveying time of day information and rotatable about the center axis.

In the embodiment where an external transmitter is provided, the wearable electronic device conveys information that is transmitted via a signal being transmitted by a transmitter. As such, the wearable electronic device will thus comprise a receiver for receiving the signal from the transmitter and a controller, operatively coupled to the receiver, for receiving and processing the signal, wherein the actuation mechanism rotates the at least one display hand in a clockwise and/or counterclockwise direction in predefined increments based at least in part on the signal being received by the receiver and transmitted by the transmitter.

It should thus also be understood that the present invention also includes a system that would comprise the transmitter for transmitting the signal, and a wearable electronic device for conveying information in an analog manner, wherein the information is conveyed via the signal being transmitted by the transmitter.

It will thus be seen that the present invention is both patentably different from and a significant improvement over the cited prior art timepieces. Specifically, the present invention provides a unique way to clearly display, and makes easily comprehensible, information relating to external parameters, as well as time-based or nontime-based information that may be programmed into or otherwise stored in the timepiece. Additionally, the present invention can incorporate a wide range of sensor circuits and arrangements for measuring external parameters and have such measurements clearly displayable and easily comprehensible, and provides an improved method, approach and thus construction to display whatever inputs it receives from the sensors. A platform for using one or more interconnectable sensors to display various functions and parameters of the human body, as described in U.S. Pat. Nos. 4,407,295 or 6,314,058, is also thus provided.

Furthermore, other features can be incorporated into the present invention, to make it even more versatile and advantageous than other devices found in the prior art. For example, because of the present invention's versatility in displaying multiple parameters on one display, the present invention incorporates unique auto calibration algorithms and constructions to ensure that the display hands are always positioned correctly.

Figure 12:
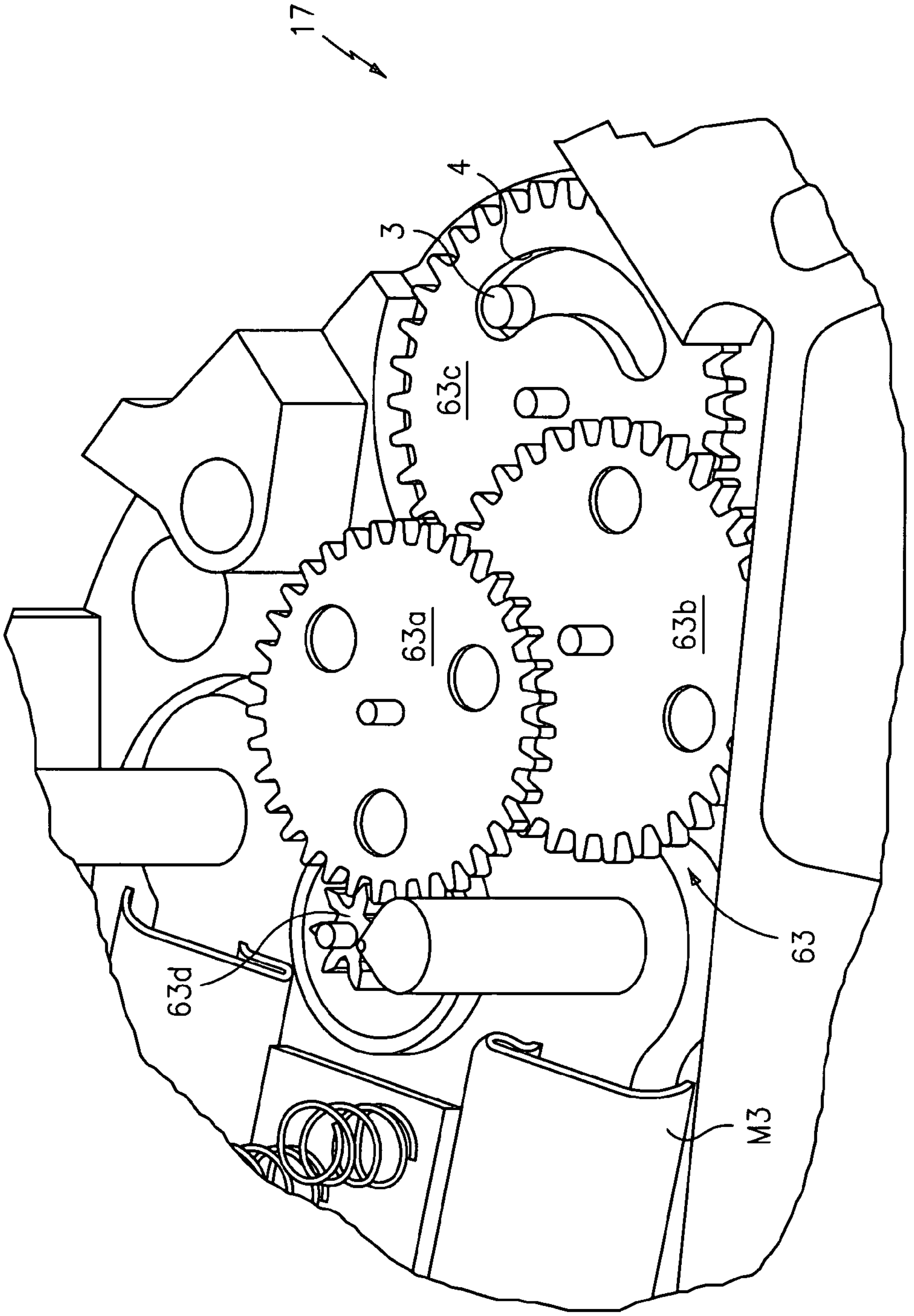
FIG. 12 is an enlarged view of the gear train for one of the non-center mounted display hands, such as display hand 24 or 26 illustrating a preferred construction for implementing an autocalibration feature.
Figure 13:
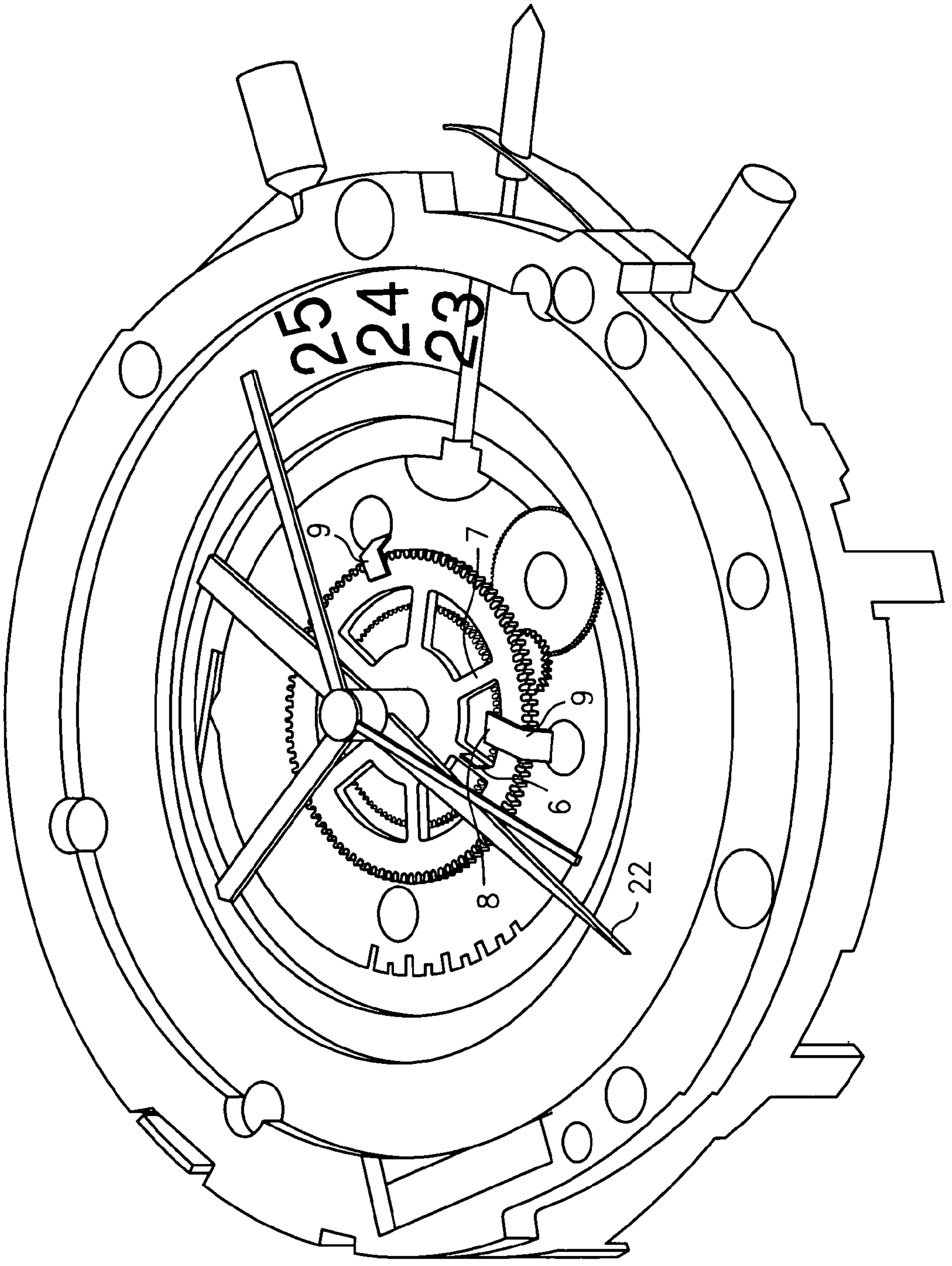
FIG. 13 is a transparent perspective view showing an alternative embodiment of a construction that can be used in combination with a preferred methodology to carry out the autocalibration feature.

For example, reference is now made to FIGS. 12–13 for a disclosure of a preferred autocalibration methodology and corresponding preferred constructions to effectuate such autocalibration of one or more of the display hands 22, 24 and 26.

Specifically, reference is first made to FIG. 12, which is an enlarged view of preferred gear train 63 for display hand 24. An identical gear train is utilized for gear train 64. As illustrated, gear train 63 comprises a first gear 63*a*, an intermediate gear 63*b* and a third gear 63*c*, which itself preferably includes stem 25 onto which display hand 24 is mounted. As would be well understood by one skilled in the art from a review of FIG. 12, but provided herein for completeness, the rotor of stepping motor M3, by way of a rotor gear 63*d*, meshes with the outer teeth (and thus causes the rotation) of first gear 63*a*. On the underside of first gear 63*a* is a pinion (not shown) which meshes with the outer teeth (and thus causes the rotation) of intermediate gear 63*b*. Similarly, a pinion (not shown) on the underside of intermediate gear 63*b* meshes with the outer teeth (and thus causes the rotation) of third gear 63*c*. Preferably, stem 25 is formed on the underside of third gear 63*c*.

In accordance with the particulars of a first embodiment of the autocalibration feature, it can be seen that part of housing 17 includes a raised tab 3 extending therefrom and into an arcuate channel 4 formed in third gear 63*c*. Channel 4 need only have a length sufficient to permit display hand 24 to sweep fully through the arc of the provided display (i.e. display 40). For example, FIG. 1 illustrates displays 40, 50 that would require about a ±70° arc through which a display hand would need to sweep to be able to indicate information at the extremes (i.e. the minimum and maximum) of the display.

The objective is therefore to provide a methodology to ensure that display hand 24 (or display hand 26 as the case may be) can be "parked" at a particular position, thereby providing the ability to recalibrate the position of the display hand, thus ensuring accurate displaying of information and providing the controller an easy way to "know" the location of the display hands, especially after calibration.

Specifically, it is preferable to rotate third gear 63*c* sufficiently to ensure that the edge of channel 4 is "pinned" against and abutting tab 3. Ensuring this sufficient rotation and "pinning" of channel 4 against tab 3 is achieved by rotating, and attempting to overrotate to some extent, third gear 63*c*. Doing so is achieved by trying to overrotate rotor gear 63*d* by several steps. It should be understood that trying to rotate rotor gear 63*d* when third gear 63*c* is already "pinned" will not damage the motor, i.e. motor M3. It should also be understood by those skilled in the art that once "pinned" by the methodology below, with bi-polar stepping motors it is advantageous to supply a defined number, such as at least two impulses for two steps in the forward direction. Then the motor is in a free rest position and the hand is in a defined position (e.g. zero position).

Before turning to the preferred methodology, it should be understood that several values must be stored in memory, such as in controller 100. For example, the maximum number of steps needed from a zero position on the display to the maximum value on the display shall be stored in memory and shall be represented by the value of "s." This value of "s" represents the maximum number of steps that the rotor would have to make so that the display hand, should it be pointing to the maximum value of the display, could sweep back to the zero position. The number of steps needed from the zero position on the display to the position such that channel 4 in third gear 63*a* would be "pinned" up against tab 3 shall also be stored in memory and shall be represented by the value of "n." A mere precautionary predetermined number of additional steps, such as several, shall be stored and represented by the value of "p." Accordingly, it can be seen that the total number of steps, represented by the quantity "K," represents the total number of steps that it is desirable to rotate rotor gear 63*d* of motor M3 to ensure that third gear 63*a* has been rotated fully to its "end stop" position. Thereafter, as will be seen below, the rotor of motor M3 and hence third gear 63*c*, can be rotated in the opposite direction "n" steps to ensure that the hand is now at the zero position.

Specifically, with the counter value "count" initialized, the rotor of motor M3 is stepped a predetermined number of steps, such as 1. The counter is then incremented by one, and it is determined whether the counter is still less than the value of "K." If it is still less than "K", it is desirable to again step the rotor of motor M3 the predetermined number of steps, increment the counter by one, and again determine whether the counter is still less than the value "K." Until the counter value is equal to "K," the rotor of motor M3 will continue to be stepped.

On the other hand, once "count" equals "K" it can be assumed that the channel edge of channel 4 is pinned against tab 3, and gear 63*c* can rotate no further in the "zeroing" direction. Thereafter, the rotor of motor M3 is rotated in the opposite direction "n" steps to place display hand 24 at the zero position (see FIG. 1), at which point the autocalibration of a display hand would be complete. Again, for bi-directional motors with rotors that make 180° rotations per step, after having third gear 63*c* "pinned," it is advantageous to step the rotor 2 steps to ensure that the rotor is thereafter able to freely rotate.

The foregoing construction is most advantage when the rotation of the gear at issue, such as third gear 63*c*, is somewhat restricted, such as the aforementioned ±70° of rotation. With such a limited rotational sweep, channel 4 need not be too long and is quite easy to form therein. However, in the event that the display hand can sweep through a larger arc (such as in the case of a heartrate monitor where display hand 22 sweeps from about the 7:00 position to the 5:00 position (about 330°)), the channel and tab configuration of FIG. 12, although adequate, is less than preferred.

In this situation, with reference being made to FIG. 13, a more practical approach is to provide a tab 6 on the gear, such as gear 7, that rotates display hand 22. Such a tab may be formed of an upwardly bent piece of gear 7 itself. Since gear 7 is preferably made of metal, a simple bending of a corner thereof is quite easy. A corresponding stopper 8 may be formed on an extending member, such as brace member 9, or other stationary member in the module, which, at the end position, as defined above, would likewise "stop" the rotation of gear 7. As would now be understood, gear 7, part of the gear train that rotates display hand 22, can only rotate about a confined 330° since the edges of stopper 8 prevent further rotation thereof. The aforementioned methodology is equally applicable to this embodiment, since the same principles apply, the only difference being whether a tab and stopper arrangement is used or a tab and channel, as disclosed. Clearly however, both of the embodiments of FIGS. 12 and 13 will work for either gear, namely 63*c* or 7, the only difference being the desirability and/or practicality of forming an elongated channel around essentially the entire gear 7, especially when it is preferably made of metal.

It can thus be seen that such an autocalibration feature is quite advantageous and novel over the known prior art, in which a display hand, such as a chronograph hand for example, needs to be calibrated by manual movement of the hand to the desired "0" position. The present invention overcomes this deficiency by providing autocalibration (or "zeroing" of the hand with one push of a button, or the like).

Still further, such as with the heart rate monitor embodiment of FIGS. 9A and 9B, a replay function is possible where a user could, at a later time, replay a running or other exercise event while the device was being worn. In this case, electronic device 10 would have a memory mode to store the parameter readings for later replay. In such a multimode/display embodiment, a user could, after the exercise activity was over, simultaneously view his/her heartrate (i.e. with hand 22 on display 45), while viewing his/her blood pressure or respiration (i.e. with hand 26 on display 50) during a time period of the run/event (i.e. with hand 24 on display 40).

Yet further, the subject matter of coowned U.S. Pat. Nos. 5,305,291 and 5,742,565 which is thus incorporated by reference as if fully set forth herein, could be integrated with the present invention to provide yet additional advantages. For example, a turning bezel could be implemented with the heart rate monitor disclosed herein, such that present invention could be providing an audible alarm when the user's heart rate was outside of the target zone that the user set. One implementation of this feature would be to permit the turning bezel ring to move markers that would make contact with display hand 22. Another embodiment would have the turning bezel ring drive a mechanism so as to communicate its position to the controller, thus providing a wide range of options using the bezel ring to provide information to the controller. Another embodiment would include a target zone setting mode, where the user could turn the bezel ring or crown and display hand 22 would move to indicate and set the zone limits.

Additionally, even if not operatively coupled to the controller, a rotating bezel may be advantageous in the embodiments wherein display hand 22 is used, since, it can be used for pointing to informational indicia on the bezel. For example, in the heartrate monitor, the bezel may be used to indicate a target heart rate zone. The user could turn the bezel to set his/her zone and then see, at a glance, what his/her heart rate is relative to that zone. In the embodiment where display hand is indicating direction, turning the bezel allows the user to have the compass hand point to north or to set a desired heading at 12 o'clock, as would be done for a handheld compass. For the electronic device that measures altitude, the bezel may be used for relative altitude. The user can turn the bezel until the altimeter hand points to zero and then track his change in altitude from that point.

While the invention has been particularly shown and described with respect to preferred embodiments thereof, it will be understood by those skilled in the art that changes in form and details may be made therein without departing from the scope and spirit of the invention.

For example, the multipurpose platform disclosed herein is applicable to the display of a wide range of additional parameters using a wide range of additional sensors, such as but not limited to, water pressure, water depth and oxygen left in a diver's tank (i.e. a diver's watch); air pressure and moisture (i.e. a weather watch); object finder (i.e. to find one's car or way back to a starting location); blood/sugar levels (a glucometer); speed and distance (a runner's watch); displaying how much money is in a debit account; and any combination of the foregoing, since the novelty lies in the multidisplay capabilities of the present invention. As set forth above, multiple sensors can provide for a plurality of displays, while multipurpose displays (such as an LCD screen) expand the number of displays possible in one display area (i.e. in display area 40, 45 and/or 50).

What is claimed is:

1. A wearable electronic device for conveying information in an analog manner at least in part by the use of at least one display hand rotatable about an axis, wherein the wearable electronic device includes a dial having a dial side and an actuation mechanism side, and the display hand is positioned on the dial side of the dial, wherein the information is transmitted via a signal being transmitted by a transmitter over a wireless link, the transmitter being physically separated from the wearable electronic device, wherein the wearable electronic device comprises:

a receiver for receiving the signal from the transmitter;

a controller, operatively coupled to the receiver, for receiving and processing the signal;

an actuation mechanism, operatively coupled to the controller, for rotating the at least one display hand in at least one of a clockwise and counterclockwise direction in predefined increments, wherein the increments and direction of the rotation of the at least one display hand are based at least in part on the signal being received by the receiver and transmitted by the transmitter;

wherein the positioning of the display hand as it rotates in the one of the clockwise and counterclockwise directions in predefined increments conveys information relating to the signal being received by the receiver; and wherein the transmitter is located in a cheststrap, and wherein the signal being received is a function of a heartrate being measured by a sensor in the cheststrap, and wherein the display hand rotates in one of the clockwise and counterclockwise direction and in predefined increments as a function of the heartrate being measured.

2. A wearable electronic device for conveying information in an analog manner at laser in part by the use of at least one display hand rotatable about an axis, wherein the wearable electronic device includes a dial having a dial side and an actuation mechanism side, and the display hand is positioned on the dial side of the dial, wherein the information is transmitted via a signal being transmitted by a transmitter physically separated from the wearable electronic device, wherein the wearable electronic device comprises:

a receiver for receiving the signal from the transmitter;

a controller, operatively coupled to the receiver, for receiving and processing the signal;

an actuation mechanism, operatively coupled to the controller, for rotating the at least one display hand in at least one of a clockwise and counterclockwise direction in predefined increments, wherein the increments and direction of the rotation of the at least one display hand are based at least in part on the signal being received by the receiver and transmitted by the transmitter;

wherein the positioning of the display hand as it rotates in the one of the clockwise and counterclockwise directions in predefined increments conveys information relating to the signal being received by the receiver; and wherein the wearable electronic device has a center stem about which rotates at least an hour hand and a minute hand, wherein the display hand is mounted on the center stem, and wherein the wearable electronic device includes indicia relating to heartrate, and wherein the positioning of the display hand on the dial is indicative of the heartrate being measured.

3. A wearable electronic device for conveying information in an analog manner at least in part by the use of at least one display hand rotatable about an axis, wherein the wearable electronic device includes a dial having a dial side and an opposing side, and the display hand is positioned on the dial side of the dial, wherein the information is conveyed via a signal being transmitted by a transmitter located in a cheststrap and physically separated from the wearable electronic device, wherein the wearable electronic device comprises:

a receiver for receiving the signal from the transmitter, wherein the signal being received is a function of a heartrate being measured by a sensor in the cheststrap;

a controller, operatively coupled to the receiver, for receiving and processing the signal;

means, operatively coupled to the controller, for rotating the at least one display hand in at least one of a clockwise and counterclockwise direction in predefined increments, wherein the increments and direction of the rotation of the at least one display hand are based at least in part on the signal being received by the receiver and transmitted by the transmitter;

wherein the positioning of the display hand as it rotates in the one of the clockwise and counterclockwise directions in predefined increments conveys information relating to the signal being received by the receiver.

4. The wearable electronic device as claimed in claim 3, wherein the electronic device is a timepiece.

5. A system for conveying information to a user, the system comprising:

a transmitter for wirelessly transmitting a signal, wherein the transmitter is located in a cheststrap, and wherein the signal being received is a function of a heartrate being measured by a sensor in the cheststrap; and a wearable electronic device physically separated from the transmitter for conveying information in an analog manner at least in part by the use of at least one display hand rotatable about an axis, wherein the wearable electronic device includes a dial having a dial side and an actuation mechanism side, and the display hand is positioned on the dial side of the dial, wherein the information is conveyed via the signal being transmitted by the transmitter, wherein the wearable electronic device comprises:

a receiver for receiving the wirelessly transmitted signal from the transmitter;

a controller, operatively coupled to the receiver, for receiving and processing the signal;

an actuation mechanism, operatively coupled to the controller, for rotating the at least one display band in at least one of a clockwise and counterclockwise direction in predefined increments, wherein the increments and direction of the rotation of the at least one display hand are based at least in part on the signal being received by the receiver and transmitted by the transmitter;

wherein the positioning of the display hand as it rotates in the one of the clockwise and counterclockwise directions in predefined increments conveys information relating to the signal being received by the receiver.

* * * * *

UNITED STATES PATENT AND TRADEMARK OFFICE

CERTIFICATE OF CORRECTION

PATENT NO. : 7,113,450 B2
APPLICATION NO. : 10/441417
DATED : September 26, 2006
INVENTOR(S) : Michel G. Plancon et al.

It is certified that error appears in the above-identified patent and that said Letters Patent is hereby corrected as shown below:

Column 23, Line 57, delete “laser” and replace it with --least--

Column 25, Line 2, delete “band” and replace it with --hand--

Signed and Sealed this

Twenty-sixth Day of December, 2006

JON W. DUDAS
*Director of the United States Patent and Trademark Office*